(12) United States Patent
Wang et al.

(10) Patent No.: US 8,466,296 B2
(45) Date of Patent: Jun. 18, 2013

(54) COMPOUNDS AND PROCESSES FOR PREPARING SUBSTITUTED AMINOMETHYL-2,3,8,9-TETRAHYDRO-7H-1,4-DIOXINO[2,3-E]INDOL-8-ONES

(75) Inventors: Zhe-qing Wang, East Haven, CT (US); Andrew Staab, Middletown, CT (US); Christopher Seekamp, Madison, CT (US); George P. Luke, Clinton, CT (US)

(73) Assignee: Ligand Pharmaceuticals, La Jolla, CA (US)

( * ) Notice: Subject to any disclaimer, the term of this patent is extended or adjusted under 35 U.S.C. 154(b) by 729 days.

(21) Appl. No.: 12/532,937

(22) PCT Filed: Mar. 26, 2008

(86) PCT No.: PCT/US2008/058203
§ 371 (c)(1),
(2), (4) Date: Mar. 23, 2010

(87) PCT Pub. No.: WO2008/118935
PCT Pub. Date: Oct. 2, 2008

(65) Prior Publication Data
US 2010/0217012 A1     Aug. 26, 2010

Related U.S. Application Data
(60) Provisional application No. 60/908,065, filed on Mar. 26, 2007, provisional application No. 60/954,076, filed on Aug. 6, 2007.

(51) Int. Cl.
| | |
|---|---|
| *C07D 491/052* | (2006.01) |
| *C07D 319/20* | (2006.01) |
| *C07D 303/12* | (2006.01) |
| *C07D 303/18* | (2006.01) |

(52) U.S. Cl.
USPC .......................... 548/430; 549/362; 549/560

(58) Field of Classification Search
USPC .................................. 548/430; 549/560, 362
See application file for complete search history.

(56) References Cited

U.S. PATENT DOCUMENTS

| | | | | |
|---|---|---|---|---|
| 5,302,599 | A | * | 4/1994 | Ennis et al. ................... 514/278 |
| 5,480,905 | A | * | 1/1996 | Koda et al. .................... 514/452 |
| 5,962,465 | A | | 10/1999 | Stack et al. |
| 6,800,637 | B2 | * | 10/2004 | Stack et al. ................... 514/291 |
| 6,800,648 | B2 | | 10/2004 | Tran et al. |
| 7,662,979 | B2 | * | 2/2010 | Galante ........................ 549/366 |
| 2004/0063686 | A1 | * | 4/2004 | Johnson et al. ........... 514/211.15 |
| 2005/0054709 | A1 | | 3/2005 | Dax et al. |
| 2005/0288329 | A1 | | 12/2005 | Yao et al. |
| 2007/0004702 | A1 | | 1/2007 | Zhou et al. |

FOREIGN PATENT DOCUMENTS
WO     WO 2007139998 A2 * 12/2007

OTHER PUBLICATIONS

Itazaki et al. Chemical & Pharmaceutical Bulletin, 1988, 36(9), 3387-403.*
International Search Report of the International Searching Authority, International Application No. PCT/US2008/058203, International Filing Date: Mar. 26, 2008, Date of Mailing: Jul. 28, 2008, 4 Pages.
Written Opinion of the International Searching Authority, International Application No. PCT/US2008/058203, International Filing Date: Mar. 26, 2008, Date of Mailing: Jul. 28, 2008, 10 Pages.

* cited by examiner

*Primary Examiner* — Jason M Nolan
(74) *Attorney, Agent, or Firm* — Cantor Colburn LLP

(57) ABSTRACT

Processes and intermediates are provided for the preparation of substituted aminomethyl 2,3,8,9-tetrahydiO-7H-1,4-dioxino[2.3-e]indo]-8-ones of the Formula (A) wherein the variables n, R and $R_3$ are as described herein. Such compounds are useful, for example, as dopamine receptor agonists.

(A)

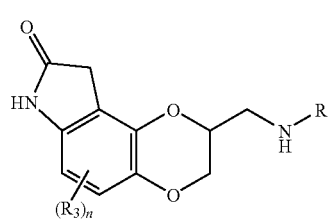

18 Claims, No Drawings

COMPOUNDS AND PROCESSES FOR PREPARING SUBSTITUTED AMINOMETHYL-2,3,8,9-TETRAHYDRO-7H-1,4-DIOXINO[2,3-E]INDOL-8-ONES

CROSS REFERENCE TO RELATED APPLICATIONS

This application is a US National Stage application filed under 35 U.S.C. §371 from PCT/US2008/058203 which is a PCT application of U.S. Provisional Application No. 60/908,065, filed Mar. 26, 2007, and U.S. Provisional Application No. 60/954,076, filed Aug. 6, 2007, each of which PCT and provisional application is hereby incorporated by reference in its entirety.

FIELD OF THE INVENTION

This invention relates generally to the synthesis of substituted aminomethyl-2,3,8,9-tetrahydro-7H-1,4-dioxino[2,3-e]indol-8-ones, which are generally dopamine D2 receptor agonists.

BACKGROUND OF THE INVENTION

The use of substituted aminomethyl-2,3,8,9-tetrahydro-7H-1,4-dioxino[2,3-e]indol-8-ones as dopamine D2 receptor agonists has been described, for example, in U.S. Pat. No. 5,756,532. That patent further provides methods for synthesizing such compounds; however, the methods described therein suffer from certain disadvantages, including the low yield and the large number of purification steps required.

Accordingly, there is a need in the art for improved methods for synthesizing substituted aminomethyl-2,3,8,9-tetrahydro-7H-1,4-dioxino[2,3-e]indol-8-ones. The present invention fulfills this need, and provides further related advantages.

SUMMARY OF THE INVENTION

The present invention generally provides intermediate compounds and processes for preparing substituted aminomethyl-2,3,8,9-tetrahydro-7H-1,4-dioxino[2,3-e]indol-8-ones of Formula A:

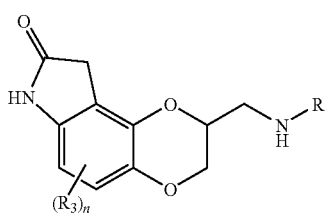

Formula A including the pharmaceutically acceptable salts and solvates (e.g., hydrates) thereof, wherein:
R is optionally substituted phenyl$C_1$-$C_2$alkyl (e.g., optionally substituted benzyl);
n is the integer 0 or 1; and
$R_3$ is a ring substituent chosen from hydroxy, halogen, $C_1$-$C_6$haloalkyl, $C_1$-$C_6$haloalkoxy, $C_1$-$C_6$alkyl, $C_1$-$C_6$alkoxy, $C_1$-$C_6$alkanoyloxy, amino, mono- or di-($C_1$-$C_6$alkyl)amino, mono- or di-($C_1$-$C_6$alkyl)aminocarbonyl and $C_1$-$C_6$alkylaminosulfonyl.

Within certain aspects, the present invention is directed to compounds of Formula 4 or a salt or hydrate thereof:

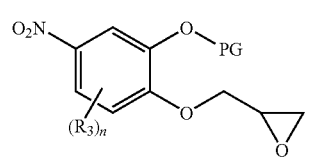

Formula 4 wherein:
n and $R_3$ are as described for Formula A; and
PG is an hydroxyl protecting group.

In other aspects, the present invention is directed to compounds of Formula 7 or a salt or hydrate thereof:

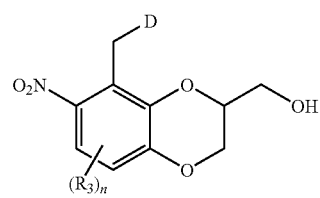

Formula 7 wherein:
n and $R_3$ are as described for Formula A;
D is COOH or —COOR$_w$; and
$R_w$ is $C_1$-$C_8$alkyl.

In other aspects, the present invention is directed to compounds of Formula 8 or a salt or hydrate thereof:

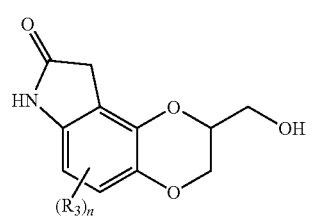

Formula 8 wherein n and $R_3$ are as described for Formula A.

In further aspects, the present invention is directed to compounds of Formula 11 or a salt or hydrate thereof:

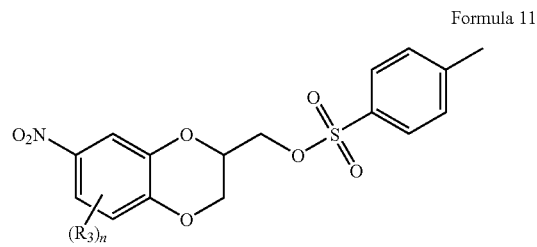

Formula 11 wherein n and $R_3$ are as described for Formula A.

In still other aspects, the present invention is directed to compounds of Formula 12 or a salt or hydrate thereof:

Formula 12

[Structure: nitro-benzodioxane with CH2-NH-R substituent, (R3)n]

wherein n, R and R₃ are as described for Formula A.

Within further aspects, the present invention is directed to processes for preparing compounds of Formula A, as described above, or a pharmaceutically acceptable salt or hydrate thereof, comprising:

reducing and cyclizing a compound of Formula 14 or a salt or hydrate thereof:

Formula 14

[Structure with R_xO-C(=O)-CH2- group, nitro, benzodioxane, CH2-NH-R, (R3)n]

wherein $R_x$ is hydrogen or $C_1$-$C_8$alkyl, and the remaining variables are as described for Formula A;

for a time and under conditions effective to provide the compound of Formula A or a pharmaceutically acceptable salt or hydrate thereof.

The present invention also provides processes for preparing compounds of Formula 4, as described above, or a salt or hydrate thereof;

comprising alkylating a compound of Formula 3 or a salt or hydrate thereof:

Formula 3

[Structure: O2N-benzene with O-PG and OH groups, (R3)n]

wherein PG, R₃ and n are as described above;

with an alkylating agent of the Formula:

[Structure: L-CH2-epoxide]

wherein L is a leaving group;

for a time and under conditions effective to provide the compound of Formula 4 or a salt or hydrate thereof.

In certain aspects, the present invention is directed to processes for preparing compounds of Formula 5 or a salt or hydrate thereof:

Formula 5

[Structure: O2N-benzodioxane-CH2OH, (R3)n]

wherein n and R₃ are as described for Formula A; comprising cyclizing a compound of Formula 4, as described above, or a salt or hydrate thereof for a time and under conditions effective to provide the compound of Formula 5 or a salt or hydrate thereof.

In other aspects, the present invention is directed to processes for preparing compounds of Formula 7, as described above, or a salt or hydrate thereof, comprising:

contacting a compound of Formula 6 or a salt or hydrate thereof:

Formula 6

[Structure: O2N-benzodioxane with CH2-W substituent and CH2OH, (R3)n]

wherein:
 W is CN or —COOR_w;
 $R_w$ is $C_1$-$C_8$alkyl; and
 n and R₃ are as described for Formula A;
with water or a $C_1$-$C_8$alkanol for a time and under conditions effective to provide the compound of Formula 7 or a salt or hydrate thereof.

In some aspects, the present invention provides processes for preparing compounds of Formula 8, as described above, or a salt or hydrate thereof, comprising reducing and cyclizing a compound of Formula 7, as described above, for a time and under conditions effective to provide the compound of Formula 8 or a salt or hydrate thereof.

In other aspects, the present invention provides processes for preparing compounds of Formula 9 or a salt or hydrate thereof:

Formula 9

[Structure: lactam-fused benzodioxane with CH2-O-tosylate group, (R3)n]

wherein n and R₃ are as described for Formula A; comprising contacting a compound of Formula 8, as described above, or a salt or hydrate thereof with toluenesulfonyl chloride for a time and under conditions effective to provide the compound of Formula 9 or a salt or hydrate thereof.

In certain embodiments, the present invention provides processes for preparing compounds of Formula A, as described above, or a pharmaceutically acceptable salt or hydrate thereof; comprising:

contacting a compound of Formula 8, as described above, or a salt or hydrate thereof with toluenesulfonyl chloride for a time and under conditions effective to provide a compound of Formula 9, as described above, or a salt or hydrate thereof; and contacting the compound of Formula 9 or salt or hydrate thereof with $RNH_2$ for a time and under conditions effective to provide the compound of Formula A or a salt or hydrate thereof.

In some aspects, the present invention provides processes for preparing compounds of Formula 11, as described above, or a salt or hydrate thereof, comprising contacting a compound of Formula 5, as described above, or a salt or hydrate thereof with toluenesulfonyl chloride for a time and under conditions effective to provide the compound of Formula 11 or a salt or hydrate thereof.

In still other aspects, the present invention provides processes for preparing compounds of Formula 12, as described above, or a salt or hydrate thereof, comprising contacting a compound of Formula 11, as described above, or a salt or hydrate thereof with $RNH_2$ for a time and under conditions effective to provide the compound of Formula 12 or a salt or hydrate thereof.

In certain aspects, the present invention is directed to processes for preparing compounds of Formula 13 or a salt or hydrate thereof:

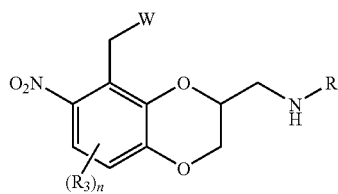

Formula 13 wherein:
n, R and $R_3$ are as described for Formula A;
W is CN or $—COOR_w$; and
$R_w$ is $C_1$-$C_8$alkyl;
comprising:
contacting a compound of Formula 12, as described above, or a salt or hydrate thereof with

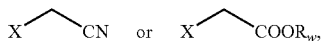

wherein X is a leaving group;
for a time and under conditions effective to provide the compound of Formula 13 or a salt or hydrate thereof.

In certain other aspects, the invention is directed to processes for preparing compounds of Formula 14, as described above, or a salt or hydrate thereof, comprising contacting a compound of Formula 13, as described above, or a salt or hydrate thereof with water or a $C_1$-$C_8$alkanol for a time and under conditions effective to provide the compound of Formula 14 or a salt or hydrate thereof.

In still other aspects, the invention is directed to processes for preparing compounds Formula A, as described above, or a pharmaceutically acceptable salt or hydrate thereof, comprising reducing and cyclizing a compound of Formula 14, as described above, or a salt or hydrate thereof for a time and under conditions effective to provide the compound of Formula A or a pharmaceutically acceptable salt or hydrate thereof.

These and other aspects of the present invention will become apparent upon reference to the following detailed description.

DETAILED DESCRIPTION OF ILLUSTRATIVE EMBODIMENTS

As employed above and throughout the disclosure, the following terms, unless otherwise indicated, shall be understood to have the following meanings.

Compounds are generally described herein using standard nomenclature. For compounds having asymmetric centers, it should be understood that (unless otherwise specified) all of the optical isomers and mixtures thereof are encompassed. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Compound descriptions are intended to encompass compounds with all possible isotopes of atoms occurring in the compounds. Isotopes are those atoms having the same atomic number but different mass numbers. By way of general example, and without limitation, isotopes of hydrogen include tritium and deuterium and isotopes of carbon include $^{11}C$, $^{13}C$ and $^{14}C$. Certain compounds are described herein using a general formula that includes variables (e.g., $R_3$, $R_x$, PG, R, W, X, D, and n). Unless otherwise specified, each variable within such a formula is defined independently of any other variable; combinations of substituents and/or variables are permissible only if such combinations result in stable compounds.

The term "substituted aminomethyl-2,3,8,9-tetrahydro-7H-1,4-dioxino[2,3-e]indol-8-one" refers to any compound that satisfies Formula A, or is a pharmaceutically acceptable salt or solvate (e.g., hydrate) of such a compound. Solvates, including hydrates, may be solvates of the compound of Formula A or may be solvates of a salt of such a compound. Unless otherwise specified, this term, and all other compound names used herein, refer both to racemic mixtures and to non-racemic compounds, and further includes any and all polymorphs.

Reference to a compound of a recited Formula or a salt or hydrate thereof (e.g., "a compound of Formula 4 or a salt or hydrate thereof") is intended to encompass compounds that satisfy the formula as drawn, hydrates of such compounds, salts of such compounds and hydrates of salts of such compounds. In certain embodiments, such salts are pharmaceutically acceptable.

A "pharmaceutically acceptable salt" of a compound recited herein is an acid or base salt that is suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutically acceptable anions for use in salt formation include, but are not limited to: acetate, 2-acetoxybenzoate, ascorbate, benzoate, bicarbonate, bromide, calcium edetate, carbonate, chloride, citrate, dihydrochloride, diphosphate, ditartrate, edetate, estolate (ethylsuccinate), formate, fumarate, gluceptate, gluconate, glutamate, glycolate, glycollylarsanilate, hexylresorcinate, hydrabamine, hydrobromide, hydrochloride, hydroiodide, hydroxymaleate, hydroxynaphthoate, iodide, isethionate, lactate, lactobionate, malate, maleate, mandelate, methylbromide, methylnitrate, methylsulfate, mucate, napsylate, nitrate, pamoate, pantothenate, phenylacetate, phosphate, polygalacturonate, propionate, salicylate, stearate, subacetate, succinate, sulfamate, sulfanilate, sulfate, sulfonates including besylate (benzenesulfonate), camsylate (camphorsulfonate), edisylate (ethane-1,2-disulfonate), esylate (ethanesulfonate) 2-hydroxyethylsulfonate, mesylate (methanesulfonate), triflate (trifluoromethanesulfonate) and tosylate (p-toluenesulfonate), tannate, tartrate, teoclate and triethiodide. Similarly, pharmaceutically acceptable cations for use in salt formation include, but are not limited to ammonium, benzathine, chloroprocaine, choline, diethanolamine, ethylenediamine, meglumine, procaine, and metals such as aluminum, calcium, lithium, magnesium, potassium, sodium and zinc. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid (e.g., one or two equivalents of acid, or with one or ½ equivalents of diacid, etc.) in water or in an organic solvent, or in a mixture of the two; generally, the use of nonaqueous media, such as ether, ethyl acetate, ethanol, methanol, isopropanol or acetonitrile, is preferred.

"Phenyl$C_1$-$C_2$alkyl" refers to any of the following substituents:

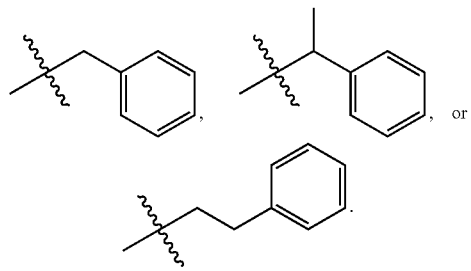

A "substituent," as used herein, refers to a molecular moiety that is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. The term "substitution" refers to replacing a hydrogen atom in a molecular structure with a substituent, such that the valence on the designated atom is not exceeded, and such that a chemically stable compound (i.e., a compound that can be isolated, characterized, and tested for biological activity) results from the substitution.

Groups that are "optionally substituted" may be unsubstituted or alternatively may be substituted by other than hydrogen at one or more available positions, typically 1, 2, 3, 4 or 5 positions, by one or more suitable groups (which may be the same or different). Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents). Other optionally substituted groups are substituted with at least one substituent (e.g., substituted with from 1 to 2, 3 or 4 independently selected substituents). Representative optional substituents include, for example, halogen, hydroxy, amino, nitro, cyano, —COOH, aminocarbonyl, aminosulfonyl, $C_1$-$C_8$alkyl, $C_2$-$C_8$alkenyl, $C_2$-$C_8$alkynyl, $C_1$-$C_8$alkoxy, $C_1$-$C_8$alkylthio, $C_1$-$C_8$haloalkyl, $C_1$-$C_8$haloalkoxy, $C_1$-$C_8$alkoxycarbonyl, $C_2$-$C_8$alkanoyloxy, and mono- and di-($C_1$-$C_8$alkyl)amino.

As used herein, the term "alkyl" refers to a straight or branched chain saturated aliphatic hydrocarbon. $C_1$-$C_8$alkyl groups include groups having from 1 to 8 carbon atoms (and all combinations and subcombinations of ranges and specific numbers of carbon atoms therein), and include methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl.

The term "alkanol" as used herein, refers to an alkane substituted with an hydroxyl group. Preferred alkanols include $C_1$-$C_8$ alkanols, (and all combinations and subcombinations of ranges and specific numbers of carbon atoms therein), such as for example, methanol, ethanol, n- and iso-propanols, iso-, and sec-, and tert-butanols, and the like and mixtures thereof.

"Alkenyl" refers to straight or branched chain alkene groups, which comprise at least one unsaturated carbon-carbon double bond. $C_2$-$C_8$alkenyl groups have from 2 to 8 carbon atoms (and all combinations and subcombinations of ranges and specific numbers of carbon atoms therein), and include ethenyl, allyl or isopropenyl. "Alkynyl" (e.g., $C_2$-$C_8$alkynyl) refers to straight or branched chain alkyne groups, which have one or more unsaturated carbon-carbon bonds, at least one of which is a triple bond.

By "alkoxy," as used herein, is meant an alkyl group as described above attached via an oxygen bridge. Alkoxy groups include $C_1$-$C_8$alkoxy, which have from 1 to 8 carbon atoms (and all combinations and subcombinations of ranges and specific numbers of carbon atoms therein). Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are representative alkoxy groups.

Similarly, "alkylthio" refers to an alkyl group as described above attached via a sulfur bridge. $C_1$-$C_8$alkylthio has from 1 to 8 carbon atoms in the alkyl portion (and all combinations and subcombinations of ranges and specific numbers of carbon atoms therein).

The term "alkoxycarbonyl" refers to an alkoxy group attached through a keto (—C(=O)—) bridge (i.e., a group having the general structure —C(=O)—O-alkyl). Alkoxycarbonyl groups include $C_1$-$C_8$alkoxycarbonyl groups, which have from 1 to 8 carbon atoms (and all combinations and subcombinations of ranges and specific numbers of carbon atoms therein) in the alkyl portion of the group (i.e., the carbon of the keto bridge is not included in the indicated number of carbon atoms). "$C_1$alkoxycarbonyl" refers to —C(=O)—O—CH$_3$; C$_3$alkoxycarbonyl indicates —C(=O)—O—(CH$_2$)$_2$CH$_3$ or —C(=O)—O—(CH)(CH$_3$)$_2$.

"Alkanoyloxy," as used herein, refers to a group having the general structure —O—C(=O)-alkyl). Alkanoyloxy groups include C$_2$-C$_8$alkanoyloxy groups, which have from 2 to 8 carbon atoms (and all combinations and subcombinations of ranges and specific numbers of carbon atoms therein). For example, "C$_2$alkanoyloxy" refers to —O—C(=O)—CH$_3$.

"C$_1$-C$_8$alkylsulfonyloxy" refers to a group of the formula —O—SO$_2$—(C$_1$-C$_8$alkyl). Similarly, C$_2$-C$_8$alkenylsulfonyloxy refers to a group of the formula —O—SO$_2$—(C$_2$-C$_8$alkenyl); and "arylsulfonyloxy" refers to a group of the formula —O—SO$_2$-aryl, such as —O—SO$_2$—(C$_6$-C$_{10}$aryl), wherein "aryl" is a cyclic group that contains only carbon ring atoms and that comprises at least one aromatic ring.

The term "aminocarbonyl" refers to an amide group (i.e., —(C=O)NH$_2$). "Mono- or di-(C$_1$-C$_6$alkyl)aminocarbonyl" refers to groups of the formula —(C=O)—N(R)$_2$, in which the carbonyl is the point of attachment, one R is C$_1$-C$_6$alkyl and the other R is hydrogen or an independently chosen C$_1$-C$_6$alkyl.

"Aminosulfonyl" refers to a group of the formula —(SO$_2$)—NH$_2$, in which the sulfur atom is the point of attachment. "Mono- or di-(C$_1$-C$_8$alkyl)aminosulfonyl" refers to a group of the formula —(SO$_2$)—N(R)$_2$, in which the sulfur atom is the point of attachment, one R is C$_1$-C$_8$alkyl and the other R is, respectively, hydrogen or an independently chosen C$_1$-C$_8$alkyl.

"Alkylamino" refers to a secondary or tertiary amine that has the general structure —NH-alkyl or —N(alkyl)(alkyl), wherein each alkyl is as described above. Such groups include, for example, mono- and di-(C$_1$-C$_8$alkyl)amino groups, in which each C$_1$-C$_8$alkyl (and all combinations and subcombinations of ranges and specific numbers of carbon atoms therein) may be the same or different.

The term "halogen" refers to fluorine, chlorine, bromine or iodine.

A "haloalkyl" is an alkyl group that is substituted with 1 or more independently chosen halogens (e.g., "C$_1$-C$_8$haloalkyl" groups have from 1 to 8 carbon atoms (and all combinations and subcombinations of ranges and specific numbers of carbon atoms therein)). Examples of haloalkyl groups include, but are not limited to, mono-, di- or tri-fluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl. Typical haloalkyl groups are trifluoromethyl and difluoromethyl. Similarly, the term "haloalkoxy" refers to a haloalkyl group as defined above attached via an oxygen bridge. "C$_1$-C$_8$haloalkoxy" groups have 1 to 8 carbon atoms.

A dash ("-") that is not between two letters or symbols is used to indicate a point of attachment for a substituent. For example, —COOH is attached through the carbon atom.

A "protecting group" is any chemical moiety introduced into a molecule by chemical modification for the purpose of protecting a reactive functional group (i.e., obtaining chemoselectivity) during a subsequent chemical reaction. The protecting group is removed in a later step, to yield the original functional group. A variety of protecting groups are commonly used in the art including, for example, acetyls, acylals, benzyl, benzyl esters (e.g., benzyloxycarbonyl), tert-butoxy carbonyl (e.g., BOC), dithianes, 9-fluorenylmethyloxycarbonyl, methoxymethyl ether, β-methoxyethoxymethyl ether, p-methoxybenzyi ether, p-methoxyphenyl, methyl esters, methylthiomethyl ether, ketals, pivaloyl, silyl esters, silyl ethers (e.g., trimethylsilyl, tert-butyldimethylsilyl, and triisopropyisilyl ethers) and tetrahydropyran. For example, an hydroxyl protecting group is any chemical moiety, such as benzyl or optionally substituted benzyl, introduced into a molecule by chemical modification for the purpose of protecting an hydroxyl functional group (i.e., obtaining chemoselectivity) during a subsequent chemical reaction. Additional information on the selection and use of protecting groups is found, for example, in T. W. Greene and P. G. M. Wuts, "*Protective Groups in Organic Synthesis*", 4$^{th}$ ed., John Wiley & Sons, Inc., Hoboken, N J (2007); and Philip J. Kocienski, "*Protecting Groups*", 2$^{nd}$ ed., John Wiley & Sons, Inc., New York (2005).

As used herein, the term "contacting" refers to the bringing together of compounds to within distances that allow for intermolecular interactions and chemical transformations accompanying such interactions. Often, contacting compounds are in solution phase.

As used herein, the term "hydrate" refers to a compound that is associated with water in the molecular form (i.e., in which the H—OH bond is not split), and may be represented, for example, by the formula R.H$_2$O, where R is a compound as described herein. A given compound may form more than one hydrate including, for example, monohydrates (R.H$_2$O) or polyhydrates (R.nH$_2$O wherein n is an integer>1) including, for example, dihydrates (R.2H$_2$O), trihydrates (R.3H$_2$O), and the like, or hemihydrates, such as, for example, R.n$_{/2}$H$_2$O, R.n$_{/3}$H$_2$O, R.n$_{/4}$H$_2$O and the like wherein n is an integer>0.

As used herein, the term "solvate" refers to a compound that is associated with solvent in the molecular form (i.e., in which the solvent is coordinatively bound), and may be represented, for example, by the formula R.(solvent), where R is a compound of the invention. A given compound may form more than one solvate including, for example, monosolvates (R.(solvent)) or polysolvates (R.n(solvent)) wherein n is an integer>1) including, for example, disolvates (R.2(solvent)), trisolvates (R.3(solvent)), and the like, or hemisolvates, such as, for example, R.n$_{/2}$(solvent), R.n$_{/3}$(solvent), R.n$_{/4}$(solvent) and the like wherein n is an integer>0. Solvents herein include mixed solvents, for example, methanol/water, and as such, the solvates may incorporate one or more solvents within the solvate. In certain embodiments, solvates provided herein are hydrates.

The term "cyclizing" or "cyclization" refers to the formation of a ring system. In certain embodiments, the cyclization methods may involve a preliminary deprotection step. For example, in embodiments involving a compound of Formula 4, the cyclization methods involve the removal of a hydroxyl protecting group followed by reaction with an adjacent glycidyloxy group to form the cyclized compound of Formula 5. The protecting group may be removed using standard deprotection techniques that are apparent to a person of ordinary skill in the art. As used herein, a "deprotecting agent" refers to any agent capable of removing an hydroxyl protecting group from a molecule resulting in conversion of the hydroxyl protected molecule into the corresponding molecule having an unprotected hydroxyl group. In certain embodiments, the protecting group is removed by a deprotecting agent, preferably a chemical deprotecting agent or a hydrogenolysis catalyst in the presence of a hydrogen source that is capable of removing the protecting group. For example, when the protecting group is an optionally substituted benzyl group, one of a class of dissolving metal reductants may be used as a chemical deprotecting agent; or a palladium, platinum, or Raney nickel catalyst may be used, for example, as a hydrogenolysis catalyst. "Hydrogenolysis catalysts", as used herein, refer to homogeneous or heterogeneous metals, either supported or unsupported, such as Pd, palladium hydroxide, Pd/C, Pt, PtO$_2$, Rh, Rh salts, Ru, Ru salts, including Raney nickel, and others known to one of skill in the art that are capable of employing hydrogen derived from a hydrogen source to convert a hydroxyl protected molecule into the corresponding molecule having an unprotected hydroxyl group. Additional examples of stoichiometric and/or catalytic deprotecting agents can be found in known treatises for the deprotection of molecules containing hydroxyl protecting groups such as "*Comprehensive Organic Transformations*" by Richard Larock, VCH Publishers, NY (1989), pages 501-504, and references cited therein, each of which is incorporated by reference herein in its entirety for its teaching of deprotecting agents and the use thereof. Further examples of chemical deprotecting agents and/or hydrogenolysis catalysts useful in removing such hydroxyl protecting groups may be found, for example, in T. W. Greene and P. G. M. Wuts, "*Protective Groups in Organic Synthesis*", 4$^{th}$ ed., John Wiley & Sons, Inc., Hoboken, N.J. (2007); and Philip J. Kocienski, "*Protecting Groups*" 2$^{nd}$ ed., John Wiley, & Sons, Inc., New York (2005). It will be apparent that the removal of a protecting group may be achieved as a separate step, or concurrently with the cyclization reaction.

As used herein, a "reducing agent" refers to any agent capable of converting a nitroarene into the corresponding aniline compound. Certain reductions employ stoichiometric reducing agents such as metal hydrides, metals in the presence of Lewis or Bronsted acids, dissolving metals and the like, including borohydrides, aluminum hydrides, tin reagents including tin hydrides, sulfides. AlH$_3$—AlCl$_3$, TiCl$_3$, Zn/acid, Sn/acid, Fe/acid, and NaBH$_2$S$_3$. Other reductions of nitroarenes to anilines may be carried out by employing a hydrogenation catalyst in the presence of a hydrogen source. As used herein, the term "hydrogen source" refers to any reagent capable of releasing hydrogen in the presence of a hydrogenation catalyst. Such hydrogen sources include hydrogen gas, hydrazine, alkanes, alkenes, cycloalkenes, formic acid, formate salts, or alcohols. Hydrogenation catalysts, as used herein refer to homogeneous or heterogeneous metals, either supported or unsupported, such as Pd, Pd/C, Pt, PtO$_2$, Rh, Rh salts, Ru, Ru salts, including Raney nickel, and others known to one of skill in the art that are capable of employing hydrogen derived from a hydrogen source to convert a nitroarene into the corresponding aniline compound. Additional examples of stoichiometric and/or catalytic reducing agents can be found in numerous known treatises for the reduction of nitro compounds, such as "*Comprehensive Organic Transformations*" by Richard Larock, VCH Publishers, NY (1989), pages 411-415, and references cited therein, each of which is incorporated by reference herein in its entirety for its teaching of reducing agents and the use thereof.

A "leaving group," as used herein, refers to an atom (or a group of atoms) capable of being displaced from a carbon atom of attachment as a stable species, taking with it the bonding electrons. In some instances, the displacing atom or group of atoms that replaces the leaving group at the carbon atom of attachment is capable of sharing some or all of its non-bonded electrons, and such replacement occurs concurrently or sequentially with the displacement of the leaving group, resulting in the formation of a new bond between the carbon atom of attachment and the displacing atom or group of atoms. Leaving groups include, for example, triflate (trifluoromethanesulfonate), p-nitrobenzoate, toluenesulfonate, mesylate, besylate, brosylate, halide, trifluoroacetate, acetate, benzoate, azide, alkoxide, aryloxide, betylate, alkyl fluorosulfonate, nonaflate, tosylate, and the like. Additional examples and further discussion of leaving groups may be found in "*Advanced Organic Chemistry*" by Jerry March, John Wiley and Sons, NY (1992) pages 352-357, and references cited therein, each of which is incorporated by reference herein in its entirety for its teaching of leaving groups and the use thereof.

Certain acidic or basic compounds of the present invention may exist as zwitterions. All forms of the compounds, including free acid, free base and zwitterions, are contemplated to be within the scope of the present invention. It is well known in the art that compounds containing both basic nitrogen atom and acidic groups often exist in equilibrium with their zwitterionic forms. Thus, any of the compounds described herein throughout that contain, for example, both basic nitrogen and acidic groups, also include reference to their corresponding zwitterions.

As noted above, the present invention generally provides intermediate compounds and processes for preparing substituted aminomethyl-2,3,8,9-tetrahydro-7H-1,4-dioxino[2,3-e]indol-8-ones of Formula A, as well as salts and solvates (e.g., hydrates) thereof.

In certain embodiments, the compound of Formula A further satisfies Formula B:

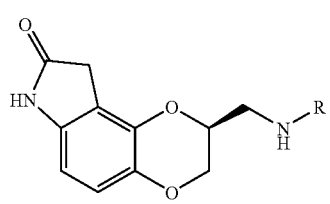

Formula B

R, in certain embodiments of Formulas A and B, is optionally substituted benzyl; in further embodiments, R is unsubstituted benzyl:

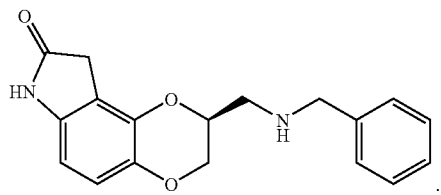

Substituted aminomethyl-2,3,8,9-tetrahydro-7H-1,4-dioxino[2,3-e]indol-8-ones provided herein are generally useful as dopamine D2 receptor agonists or partial agonists. As such, they find use in the treatment of dopaminergic disorders such as, for example, schizophrenia, schizoaffective disorder, Parkinson's disease, Tourette's syndrome, restless leg syndrome, hyperlactinemia and drug addiction. Certain such uses are described, for example, in U.S. Pat. No. 5,756,532, especially at columns 9-11 which are hereby incorporated by reference for such teaching.

In certain embodiments (e.g., in compounds of Formula A, 3, 4, 5, 6, 7, 8, 9, 11, 12, 13, or 14, or processes involving compounds of Formula A, 3, 4, 5, 6, 7, 8, 9, 11, 12, 13, or 14) R$_3$ is H, —OH, halo, polyhaloalkyl, polyhaloalkoxy, alkyl, or alkoxy; in further embodiments, R$_3$ is H, —OH, halo, polyfluoroalkyl, polyfluoroalkoxy, alkyl, or alkoxy; in still further embodiments, R$_3$ is H, —OH, trifluoromethyl, trifluoromethoxy, alkyl, or alkoxy; and in other embodiments, R$_3$ is H.

In some embodiments of compounds of Formula 3 or 4, or processes involving Formula 2, 3, or 4 compounds, PG is optionally substituted benzyl.

In certain embodiments of compounds of Formula A, 5, 12, or 13, or processes involving compounds of Formula A, 5, 12, or 13, R is optionally substituted phenylC$_1$-C$_2$alkyl; within certain such embodiments, R is benzyl.

Synthesis of Substituted Aminomethyl-2,3,8,9-tetrahydro-7H-1,4-dioxino[2,3-e]indol-8-ones Starting materials for the methods provided herein are commercially available from suppliers such as Sigma-Aldrich Corp. (St. Louis, Mo.), or may be synthesized from commercially available precursors using established protocols. The following Schemes illustrate certain embodiments of the present invention, and are intended to be exemplary only, and nonlimiting. For example, it will be apparent that each reaction described in a Scheme may be performed in combination with none, some or all of the other reactions described therein (e.g., step 1 could be omitted by starting with protected compound 2). In addition, various modifications to reaction conditions will be apparent, including the use of different solvents and acids/bases, and changes in reaction times and temperatures. All processes disclosed in association with the present invention are contemplated to be practiced on any scale, including milligram, gram, multigram, kilogram, multikilogram or commercial industrial scale. It will further be apparent that starting materials for each step, and each reaction product, may be the indicated compound or may be a salt (e.g., a pharmaceutically acceptable salt) or solvate (e.g., hydrate) thereof. Unless otherwise specified, each variable in the following Schemes is as defined above.

Schemes A-C illustrate the synthesis of the intermediate compound 5, which is (7-nitro-2,3-dihydrobenzo[b][1,4]dioxin-2-yl)methanol, from 2-methoxy-5-nitrophenol, or a substituted analogue thereof. In Scheme A, the variable "PG" is an hydroxyl protecting group; in certain embodiments, PG is benzyl or optionally substituted benzyl (e.g., substituted with one or more of halogen, C$_1$-C$_4$alkyl, nitro or methoxy).

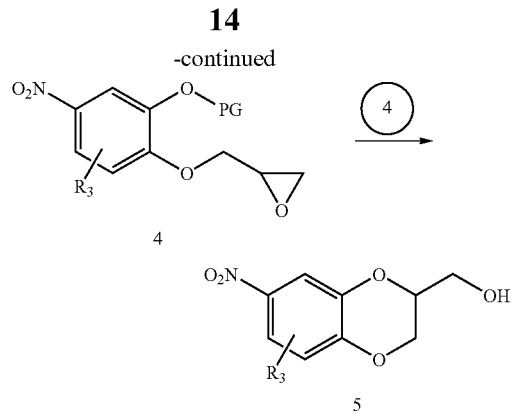

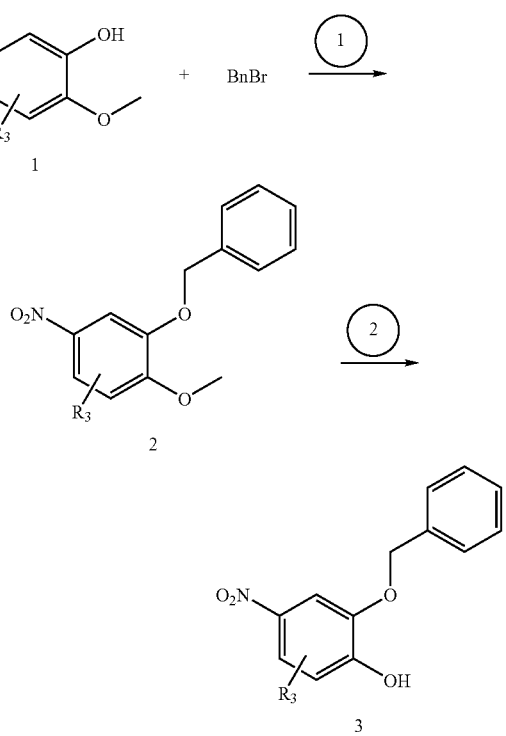

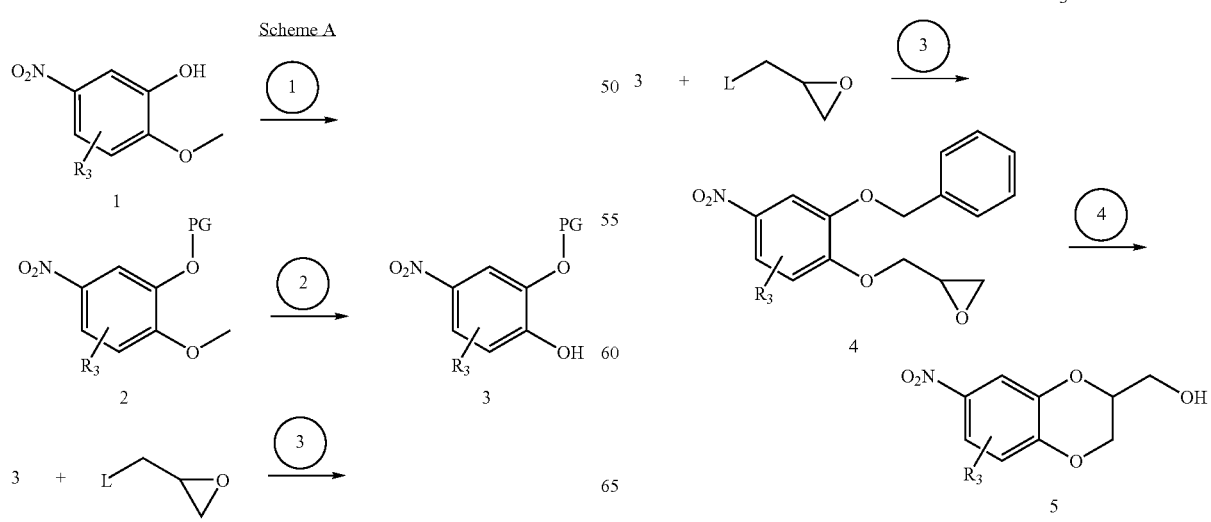

-continued

Scheme C

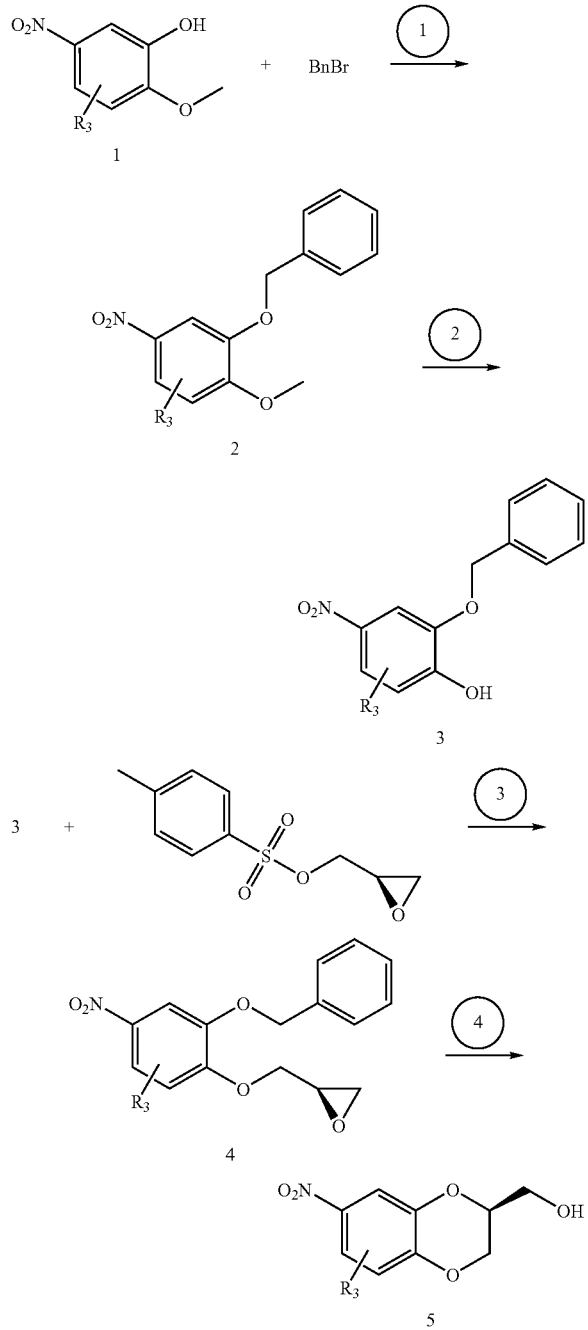

In step ① of Scheme A, the hydroxyl group of compound 1 (2-methoxy-5-nitrophenol or a salt or substituted analogue thereof) is protected with any suitable protecting group. As a non-limiting example, the use of a benzyl protecting group is shown in Schemes B and C. Step ① may be achieved by any of a variety of known methods, such as reaction with benzyl bromide or benzyl chloride in the presence of base (e.g., sodium hydroxide, potassium carbonate or cesium carbonate). In one method (illustrated in Example 1A as Method 1), the base (typically from about 1 to about 1.5 molar equivalents, preferably about 1 molar equivalent) is added to compound 1, preferably in a solvent, preferably such as DMF, under an inert atmosphere, preferably nitrogen, and then benzyl bromide or benzyl chloride (e.g., about 1 molar equivalent) is added to the basic solution. The resulting mixture is heated (e.g., to a temperature ranging from about 50° C. to about 80° C. for about 12 to about 36 hours). The solution is then generally cooled (e.g., to room temperature) and compound 2 generally forms as a precipitate upon the addition of water. In an alternate method (illustrated in Example 1A as Method 2), aqueous base (typically from about 2 to about 5 molar equivalents, preferably about 3 to about 4, with about 3.5 equivalents being even more preferred) is added to compound 1 in a solvent such as toluene under nitrogen, and then benzyl bromide (e.g., about 1 molar equivalent) is added to the basic solution. The resulting suspension converts to a two phase solution upon heating (e.g., about 50 to about 55° C. for at least about an hour). Additional heating (e.g., about another 2 to about 3 hours) completes the reaction, whereupon the organic phase contains compound 2. It will be apparent that different solvents (e.g., acetone, acetonitrile or THF (THF/water in method 2)) or bases may be appropriate, although triethylamine has been found to be unsuitable for Method 1. If benzyl chloride is used, the procedure illustrated in Method 1 is preferred. Alternatively, the sodium salt of 2-methoxy-5-nitrophenol can be used in step ① in combination with benzyl chloride and potassium carbonate to generate the benzyl-protected intermediate. In Schemes B and C, 2-(benzyloxy)-1-methoxy-4-nitrobenzene or a substituted analogue thereof (compound 2) is generally obtained in crystalline form. Compound 2 in Scheme A is also referred to herein as a compound of Formula 2. In certain embodiments, $R_3$ is absent (i.e., n is the integer 0); in further embodiments, compound 2 is 2-(benzyloxy)-1-methoxy-4-nitrobenzene.

Step ② is a demethylation reaction, in which the methoxy group of compound 2 is converted to a hydroxy group. Various demethylation reactions will be apparent to those of ordinary skill in the art, including those described in Wuts and Greene, *Greene's Protective Groups in Organic Synthesis*, 4th ed., John Wiley & Sons, Inc., Hoboken, N.J. (2007). Demethylation may be achieved, for example, by heating in the presence of base (e.g., a hydroxide such as NaOH or KOH). Briefly, base (typically from 2 to 3 molar equivalents) is added to compound 2 in a solvent such as DMSO and the solution is heated (e.g., to about 80 to 90° C. for at least about 18 hours).

The solution is then cooled, water is added and the pH is adjusted to ~1 (e.g., by addition of concentrated HCl). Following extraction with an organic solvent such as toluene, compound 3 is obtained from the organic phase. Certain specific reaction and purification conditions for this step are provided in Example 1B. In reactions performed as illustrated in Schemes B and C, 2-(benzyloxy)-4-nitrophenol or a substituted analogue thereof (compound 3) is generally obtained in crystalline form. Compound 3 in Scheme A is also referred to herein as a compound of Formula 3. In certain embodiments, $R_3$ is absent (i.e., n is the integer 0); in further embodiments, compound 3 is 2-(benzyloxy)-4-nitrophenol; in still further embodiments, compound 3 is obtained as a phenolate salt (e.g., the potassium phenolate).

In step

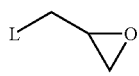

compound 3 is alkylated with an alkylating agent of the formula:

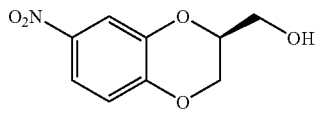

in which L is a leaving group such as a halogen (e.g., chloride), optionally substituted $C_1$-$C_8$alkylsulfonyloxy (e.g., optionally substituted methanesulfonyloxy), optionally substituted $C_2$-$C_8$alkenylsulfonyloxy or optionally substituted arylsulfonyloxy (e.g., tosyloxy, triflyloxy, nitrophenylsulfonyloxy such as 3- or 4-nitrophenylsylfonyloxy or bromophenylsulfonyloxy). In certain embodiments, the alkylating agent is the (R)-glycidyl isomer. In Schemes A and B, the variable "L" is, for example, Br or 4-methylbenzenesulfonate. Representative alkylating agents include, for example, glycidyl tosylate, such as (R)-glycidyl tosylate or (S)-glycidyl tosylate, and the racemic epibromohydrin). As shown in Scheme C, if the desired compound 5 is (S)-(7-nitro-2,3-dihydrobenzo[b][1,4]dioxin-2-yl)methanol:

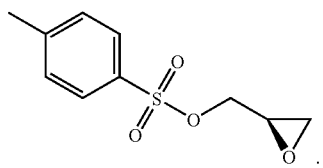

then the alkylating agent is (R)-glycidyl tosylate:

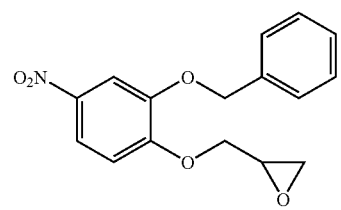

Briefly, compound 3, the alkylating agent (typically from about 1.0 to about 1.5 molar equivalents) and a base (e.g., potassium carbonate, cesium carbonate or sodium hydroxide; typically from about 1.1 to about 1.5 molar equivalents) are heated in a solvent (e.g., DMF, acetone, acetonitrile or toluene) to a temperature ranging from about 45 to about 70° C.

After the reaction is complete (about 18 hours at about 60° C. is generally sufficient), the solution is cooled and water is added to form a suspension of compound 4, which is isolated by standard procedures. Certain specific reaction and purification conditions for this step are provided in Example 1C. In certain embodiments, $R_3$ is absent (i.e. n is the integer 0); in further embodiments, compound 4 is 2-((2-(benzyloxy)-4-nitrophenoxy)methyl)oxirane:

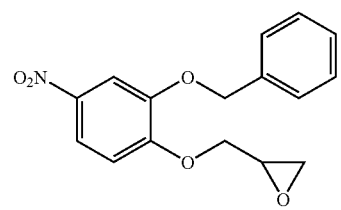

In Scheme C, compound 4 is (R)-2-((2-(benzyloxy)-4-nitrophenoxy)methyl)oxirane.

Alternatively, as illustrated in Example 1D, compound 4 is prepared by way of a nitrophenolate intermediate. Briefly, in one such embodiment, compound 2 is heated (e.g., to a temperature ranging from about 80 to about 100° C. for about 8 to about 24 hours) preferably in a solvent, preferably such as DMSO, and in the presence of base (e.g., 3 to 10 N NaOH). The internal temperature during the heating step preferably reaches about 95° C. After the heating step, the solution is cooled (e.g., to a temperature ranging from about 20 to about 30° C.), pH is adjusted to between about 7 and about 8 (e.g., with HCl), and toluene or MTBE is added. The mixture is then acidified to a pH between about 1 and about 2 (e.g., with HCl), layers are allowed to separate and the toluene phase contains the desired product. Washing and distillation yields a concentrated solution, which is then added to a warm (e.g., 40 to 45° C.) solution of isopropanol and potassium hydroxide, resulting in the formation of a precipitate. The slurry is cooled (e.g., to a temperature ranging from about 20 to about 25° C.) and precipitate is collected by filtration. The potassium nitrophenolate is then heated with alkylating agent such as glycidyl tosylate (typically from about 1.0 to about 1.5 molar equivalents) in a solvent (e.g., DMF) to a temperature ranging from about 45 to about 70° C. After the reaction is complete (about 18 hours at about 65° C. is generally sufficient), the solution is cooled and water is added to form a suspension of compound 4, which is isolated by standard procedures.

The cyclization in step

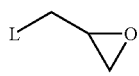

is achieved, for example, by reaction with a carbonate (e.g., sodium carbonate, sodium bicarbonate or potassium carbonate) in ethanol. Briefly, compound 4 is combined with ethanol, the carbonate (typically from about 1 to about 3 molar equivalents) and 1,4-cyclohexadiene (typically from about 1.5 to about 3 equivalents). In certain embodiments, an inert atmosphere, such as argon gas, is bubbled through the suspension (e.g., for 5 min), and then the bubbling is discontinued and a deprotecting agent such as palladium on carbon (e.g., about 5%, about 10% or about 20%, any of which may be wet or dry), Raney nickel, a platinum catalyst or a chemical deprotecting agent is added. The mixture is heated to a temperature ranging from about 50 to about 70° C. and stirred. Compound 5 is readily obtained upon removal of the catalyst and evaporation of the solvent. Certain specific reaction and purification conditions for this step are provided in Example 1E. In Schemes B and C, (7-nitro-2,3-dihydrobenzo[b][1,4]dioxin-2-yl)methanol or a substituted analogue thereof (compound 5) is generally obtained in crystalline form. Compound 5 in Scheme C is (S)-(7-nitro-2,3-dihydrobenzo[b][1,4]dioxin-2-yl)methanol, or a substituted analogue thereof. In certain embodiments, $R_3$ is absent (i.e., n is the integer 0); in further embodiments, Compound 5 is (7-nitro-2,3-dihydrobenzo[b][1,4]dioxin-2-yl)methanol.

Alternatively, step

④ is achieved using $H_2$ gas and a catalyst such as palladium, platinum, each preferably on a support, or Raney nickel. Briefly, compound 4 is combined with base (e.g., sodium bicarbonate, sodium carbonate, potassium carbonate, potassium bicarbonate; typically from about 0.5 to about 3 equivalents) and catalyst (e.g., palladium on carbon about 5 to about 20% or palladium hydroxide on carbon 5 to about 20%; typically with a catalyst load of about 3 to about 10% w/w dry basis (about 6 to about 20% w/w wet)) in solvent such as ethanol, or a mixture of ethanol and N-methylpyrrolidone (NMP). The mixture is heated (preferably to between 50 and 60° C.) and then hydrogen gas is titrated into the solution. Heating is discontinued and nitrogen is bubbled through the solution. The cooled (e.g., to about 25° C.) solution is filtered through Celite and the filter cake is washed (e.g., with ethanol). The resulting solution is concentrated, and then water is slowly added, resulting in formation of a precipitate. After stirring (e.g., for about 3 to about 72 hours), the precipitate (compound 5) is collected by standard techniques. Alternatively, if a mixture of ethanol and NMP is used, the ethanol is removed by distillation, isopropyl acetate and water are added to the resulting solution and the product (compound 5) is extracted into isopropyl acetate layer. Compound 5 need not be isolated prior to step 11 (Scheme II). The isopropyl acetate is removed by distillation, exchanged to pyridine and the tosyl chloride is added. Certain specific reaction and purification conditions for this step are provided in Example 1F.

Step

④ may also be achieved using formate and formic acid and a catalyst such as palladium, platinum, each preferably on a support, or Raney nickel. Briefly, compound 4 is combined with a solvent such as methanol, ethanol, NMP, DMF, or mixtures thereof and catalyst (e.g., palladium on carbon, about 5 to about 20%; typically with a catalyst load of about 3 to about 10% w/w/dry basis (about 6 to about 20% w/w wet)). The mixture is heated to between 40 and 78° C., and then a solution of a formate (e.g., sodium formate, typically from about 0.05 to about 1 equivalent) in formic acid (e.g., 95% formic acid; typically from about 1 to about 3 equivalents) is added. Upon complete consumption of the starting material it may be beneficial to adjust the pH of the reaction mixture to a pH of about 9 by addition of base (e.g., NaOH; typically a 1 N aqueous solution). Heating is discontinued and then the cooled (e.g., to about 25° C.) solution is filtered through Celite and the filter cake is washed (e.g., ethanol). The resulting solution is concentrated, and then water is slowly added, resulting in formation of a precipitate. After stirring (e.g., for about 2 to about 72 hours), the precipitate (compound 5) is collected by standard techniques. Certain specific reaction and purification conditions for this step are provided in Examples 1G and 1H.

Compound 5 is then used to generate substituted aminomethyl-2,3,8,9-tetrahydro-7H-1,4-dioxino[2,3-e]indol-8-ones of Formula A. Schemes I and II illustrate two synthetic methods for such compounds. In certain embodiments, $R_3$ in Schemes I and II is absent (i.e., n is the integer 0); in further embodiments, compound 5 is (S)-(7-nitro-2,3-dihydrobenzo[b][1,4]dioxin-2-yl)methanol:

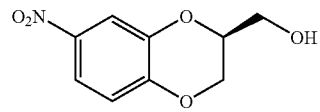 [SMILES: O=[N+]([O-])c1ccc2c(c1)O[C@@H](CO)CO2]

and the subsequent intermediates and resulting compound A are similarly non-racemic.

Scheme I

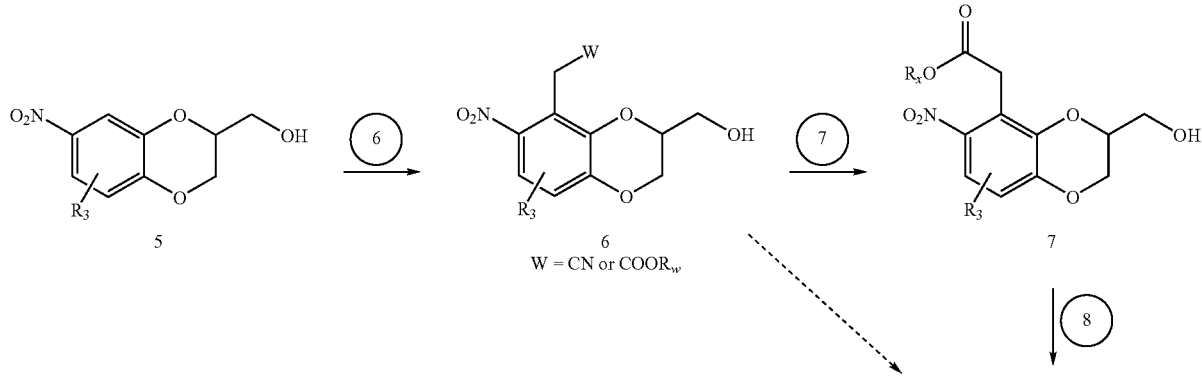

21

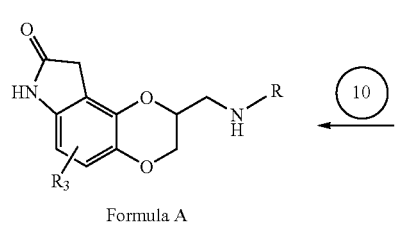

Formula A

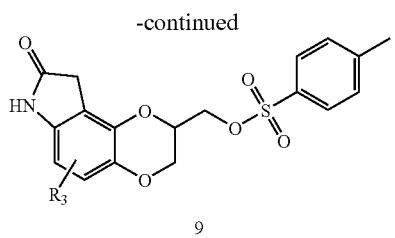

9

-continued

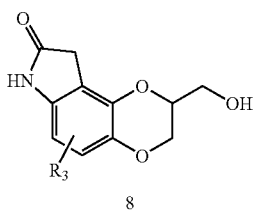

8

In step

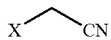

of Scheme I, compound 5 is contacted with

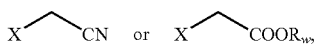

wherein X is a leaving group and $R_w$ is an alkyl group, to yield compound 6, which is 2-(3-(hydroxymethyl)-6-nitro-2,3-dihydrobenzo[b][1,4]dioxin-5-yl)acetonitrile or an alkyl 2-(3-(hydroxymethyl)-6-nitro-2,3-dihydrobenzo[b][1,4]dioxin-5-yl)acetate. A variety of leaving groups may be used in this reaction; suitable

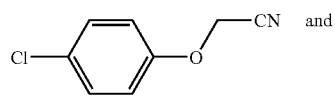

moieties include 2-(4-chlorophenoxy)acetonitrile and 2-(4-bromophenoxy)acetonitrile:

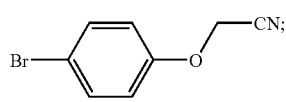

and suitable

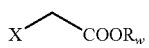

groups include, for example, tert-butyl 2-chloroacetate, tert-butyl 2-bromoacetate and ethyl 2-bromoacetate. Briefly, in one such reaction, base such as solid potassium t-butoxide, NaOH, KOH, sodium t-butoxide, sodium t-pentoxide, potas-

22 sium t-pentoxide, KHMDS, LiHMDS, NaHMDS or lithium diisopropyl amide (typically about 3 to 5 molar equivalents) in a solvent such as DMF, DMSO, or N-methyl-2-pyrrolidone is cooled to a temperature ranging from about −20 to about 25° C. Compound 5 and

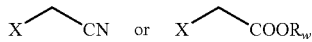

(about equimolar amounts, preferably in solvent) are then added. The reaction is quenched with an acid such as about 1 N HCl. Extraction and removal of the volatiles yields compound 6 as a residue, which is purified using standard methods. Certain specific reaction and purification conditions for this step are provided in Example 2A.

In step (7), the nitrile or ester group of compound 6 is hydrolyzed by contact with water or a $C_1$-$C_8$alkanol (e.g., by heating under acidic conditions). $R_x$ may be hydrogen (i.e., compound 14 is an acid) or $C_1$-$C_8$alkyl, such as methyl or ethyl (i.e., compound 14 is an ester). In certain embodiments, compound 7 is 2-(3-(hydroxymethyl)-6-nitro-2,3-dihydrobenzo[b][1,4]dioxin-5-yl)acetic acid or a substituted analogue thereof, such as (S)-2-(3-(hydroxymethyl)-6-nitro-2,3-dihydrobenzo[b][1,4]dioxin-5-yl)acetic acid:

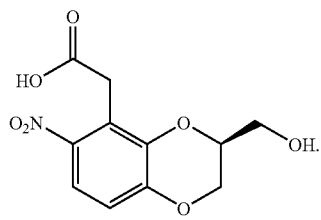 [SMILES: O=C(O)Cc1c([N+](=O)[O-])ccc2c1O[C@@H](CO)CO2]

Briefly, in a typical process, compound 6 is heated to a temperature ranging from about 80 to about 110° C. in aqueous acid solution (e.g., about 6 N HCl). After about 4 to about 18 hours, heating is discontinued and a precipitate of compound 7 forms. Compound 7 is purified using standard methods. Certain specific reaction and purification conditions for this step are provided in Example 2B. Compound 7 is also referred to herein as a compound of Formula 7.

The cyclization in step (8)

is achieved by reducing the nitro group to an amino group and cyclizing, yielding 2-(hydroxymethyl)-2,3,8,9-tetrahydro-7H-[1,4]dioxino[2,3-e]indol-8-one or a substituted analogue thereof (compound 8; also referred to herein as a compound of Formula 8). In certain embodiments, $R_3$ is absent (i.e., n is the integer 0); in further embodiments, compound 8 is (2S)-2-(hydroxymethyl)-2,3,8,9-tetrahydro-7H-[1,4]dioxino[2,3-e]indol-8-one:

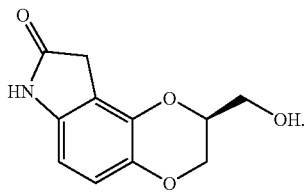 [SMILES: O=C1Cc2c(ccc3c2O[C@@H](CO)CO3)N1]

Briefly, in certain such reactions, compound 7 is hydrogenated under basic conditions in the presence of reducing agent such as palladium or platinum. Such hydrogenation typically is performed under pressure (e.g., about 15 to about 50 psig hydrogen) for about 1 to about 72 hours. The catalyst is removed and the solution is then acidified and heated to a temperature ranging from about 50 to about 80° C. After about 4 to about 24 hours, heating is discontinued and the resulting suspension contains compound 8, preferably as a precipitate, which is isolated using standard methods. Cyclization may be spontaneous following reduction of the nitro group (e.g., if $R_x$ is an alkyl group); in such instances, no additional cyclization step is required. In certain embodiments, compound 8 is isolated as a hydrate. Certain specific reaction and purification conditions for this step are provided in Example 2C.

It will be apparent, as indicated by the dotted arrow, that step (7)

may be omitted if W is an ester moiety. In such cases, compound 6 is used directly in step (8).

In step (9), compound 8 is contacted with p-toluenesulfonyl chloride (TsCl) to yield the tosylated intermediate (8-oxo-2,3,8,9-tetrahydro-7H-[1,4]dioxino[2,3-e]indol-2-yl)methyl 4-methylbenzenesulfonate or a substituted analogue thereof (compound 9). In certain embodiments, $R_3$ is absent (i.e., n is the integer 0); in further embodiments, compound 9 is [(2R)-8-oxo-2,3,8,9-tetrahydro-7H-[1,4]dioxino[2,3-e]indol-2-yl]methyl 4-methylbenzenesulfonate:

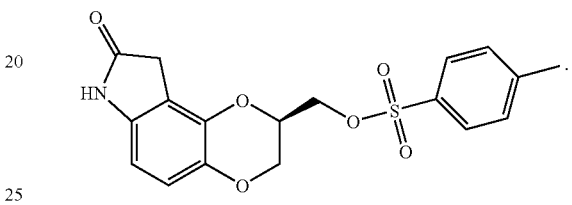

Briefly, compound 8 is dissolved in solvent (e.g., pyridine or 2-picoline) and TsCl (typically from about 1 to about 2 molar equivalents) is added, preferably with heating to a temperature ranging from about 30 to about 40° C. After about 3 to about 18 hours, an alcohol such as methanol, ethanol, isopropanol or butanol is added, forming a suspension. The precipitate (compound 9) is isolated using standard methods. Certain specific reaction and purification conditions for this step are provided in Example 2D.

Step (10)

yields the substituted aminomethyl-2,3,8,9-tetrahydro-7H-1,4-dioxino[2,3-e]indol-8-one. Briefly, compound 9 is contacted with R—$NH_2$ (e.g., benzylamine) in a solvent such as DMSO, preferably under an inert atmosphere, more preferably nitrogen, and with heating (e.g., to a temperature ranging from about 70 to about 90° C. for about 8 to about 24 hours). The substituted aminomethyl-2,3,8,9-tetrahydro-7H-1,4-dioxino[2,3-e]indol-8-one is isolated using standard methods. Certain specific reaction and purification conditions for this step are provided in Example 2E.

If desired, a salt of the substituted aminomethyl-2,3,8,9-tetrahydro-7H-1,4-dioxino[2,3-e]indol-8-one is prepared. Briefly, the substituted aminomethyl-2,3,8,9-tetrahydro-7H-1,4-dioxino[2,3-e]indol-8-one is heated in a solvent such as ethanol or isopropanol, and then the acid (generally about 1 to about 2 molar equivalents) is added, forming a mono- or hemi-salt. As the solution cools, seed crystals may be added to facilitate formation of the precipitate, which is isolated using standard methods. In certain embodiments, the salt is a pharmaceutically acceptable salt as described above. Certain specific reaction and purification conditions are provided in Example 2F.

Scheme II illustrates an alternate method for the synthesis of compounds of Formula A.

Scheme II

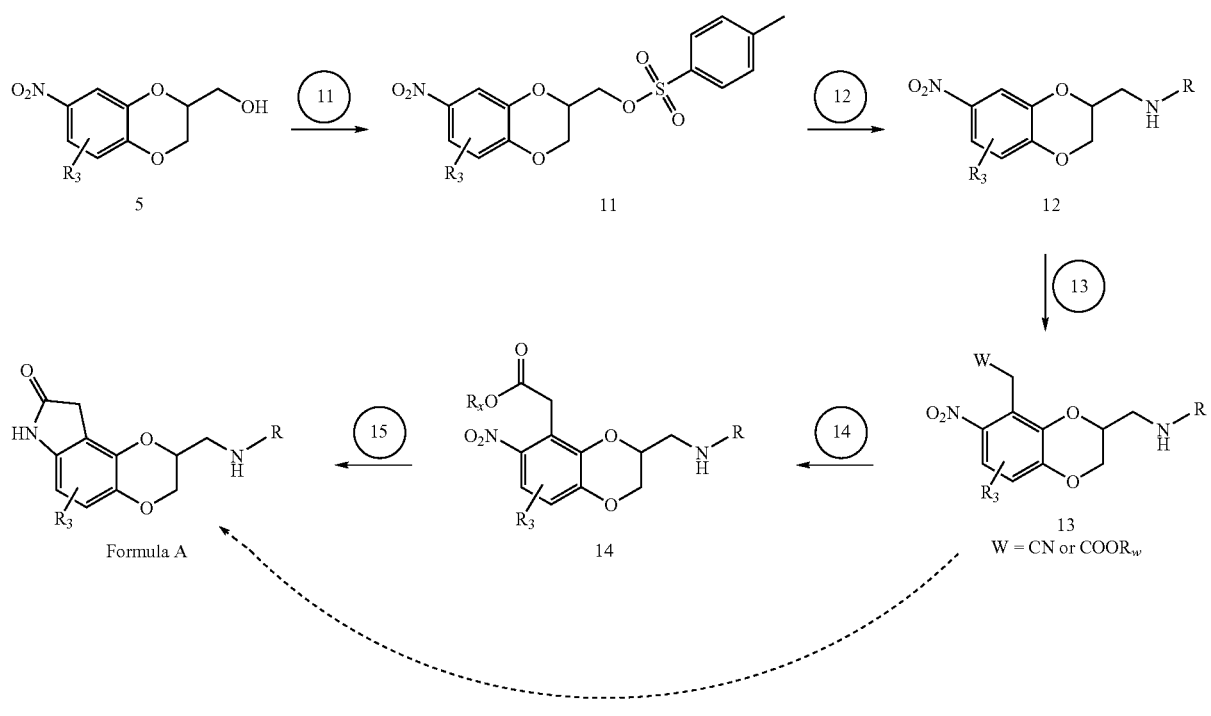

In step ⑪,

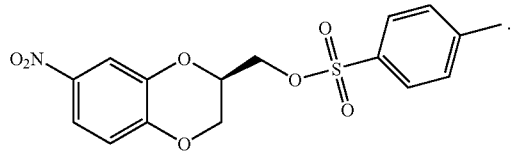 [SMILES: Cc1ccc(S(=O)(=O)OC[C@H]2COc3ccc([N+](=O)[O-])cc3O2)cc1]

of Scheme II, compound 5, in a solvent such as pyridine, is contacted with TsCl to yield (7-nitro-2,3-dihydrobenzo[b][1,4]dioxin-2-yl)methyl 4-methylbenzenesulfonate or a substituted analogue thereof (compound 11; also referred to herein as a compound of Formula 11), which is generally obtained in crystalline form. Briefly, TsCl (about 1 to about 2 molar equivalents) is added to a solution of compound 5, preferably in solvent (preferably cooled to a temperature ranging from about 0 to about 5° C.). The reaction proceeds with stirring, typically first at the reduced temperature (e.g., for about 1 to about 2 hours) and then while being allowed to warm to room temperature (e.g., for about 2 to about 12 hours). Addition of the reaction mixture to water results in the formation of compound 11, preferably as a precipitate, which is isolated using standard methods. Certain specific reaction and purification conditions are provided in Examples 3A, 3B and 3C. In certain embodiments, $R_3$ is absent (i.e., n is the integer 0); in further embodiments, compound 11 is (7-nitro-2,3-dihydrobenzo[b][1,4]dioxin-2-yl)methyl 4-methylbenzenesulfonate. If compound 5 is (S)-(7-nitro-2,3-dihydrobenzo[b][1,4]dioxin-2-yl)methanol, then compound 11 is (R)-(7-nitro-2,3-dihydrobenzo[b][1,4]dioxin-2-yl)methyl 4-methylbenzenesulfonate:

In step ⑫, compound 11 is contacted with R—NH$_2$ to yield compound 12 (also referred to herein as a compound of Formula 12) in crystalline form. If R is benzyl, compound 11 is contacted with benzylamine in this step, and compound 12 is N-((7-nitro-2,3-dihydrobenzo[b][1,4]dioxin-2-yl)methyl)(phenyl)methanamine:

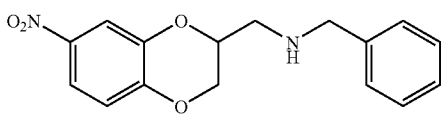 [SMILES: O=[N+]([O-])c1ccc2c(c1)OC(CNCc1ccccc1)CO2]

or a substituted analogue thereof. Briefly, a mixture of compound 11 and R—NH$_2$ is heated (e.g., to a temperature ranging from about 90 to about 100° C. for about 2 to about 6 hours). The heating may be performed without solvent, or may be performed in a solvent such as DMSO or N-methyl-2-pyrrolidone. During cooling, heptane, hexane, or water is added and compound 12 forms, preferably as a precipitate, which is isolated using standard methods. Certain specific reaction and purification conditions are provided in Examples 3D and 3E. In certain embodiments, $R_3$ is absent (i.e., n is the integer 0). In further embodiments, compound 12 is (S)—N-((7-nitro-2,3-dihydrobenzo[b][1,4]dioxin-2-yl)methyl)(phenyl)methanamine:

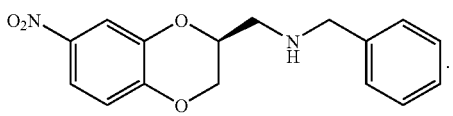 [SMILES: O=[N+]([O-])c1ccc2c(c1)O[C@@H](CNCc1ccccc1)CO2]

In certain embodiments wherein compound 12 is a mix of (R)- and (S)-stereoisomers, the mixture of isomers may be separated by standard techniques including, but not limited to, preferential salt formation. Briefly, the enantiomeric enrichment is achieved, for example, by contacting compound 12 (about 90% to about 97% ee) with a nonracemic chiral salt (e.g., (S)-mandelic acid, (R)-mandelic acid L-tartaric acid, dibenzoyl-L-tartaric acid, dibenzol-D-tartaric acid, di-p-toluoyl-L-tartaric acid, or di-p-toluoyl-D-tartaric acid) in a $C_1$-$C_8$alkanol solvent (e.g., ethanol, isopropanol, 1-butanol) at elevated temperature (e.g., about 60 to about 80° C.). Upon cooling to room temperature, the product crystallizes from solution and is collected by filtration. Certain specific reaction and purification conditions for this step are provided in Example 3F (Step 1). Free-basing of the resultant salt is achieved, for example, by contacting the salt with an aqueous base (e.g., NaOH, KOH, $Na_2CO_3$, $K_2CO_3$) in a solvent such as 2-methyltetrahydrofuran, THF, ethyl acetate, or toluene. After stirring for about 30 to about 90 minutes, the enantiomerically enriched (e.g., greater than 95% ee or greater than 99% ee) compound 12 is isolated by standard procedures. Certain specific reaction and purification conditions for this step are provided in Example 3F (Step 2). In certain embodiments, the enantiomerically enriched compound 12 is (S)-N-((7-nitro-2,3-dihydrobenzo[b][1,4]dioxin-2-yl)methyl)(phenyl)methanamine:

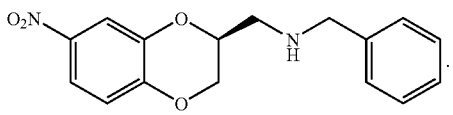 [SMILES: O=[N+]([O-])c1ccc2c(c1)O[C@@H](CNCc1ccccc1)CO2]

In step

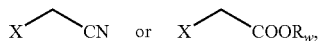

compound 12 is contacted with

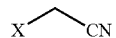 or 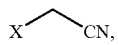

wherein X and $R_w$ are as described above, to yield compound 13 (also referred to herein as a compound of Formula 13). A variety of leaving groups may be used in this reaction; one suitable is 2-(4-chlorophenoxy)acetonitrile. If R is benzyl and compound 12 is contacted with

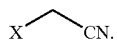

then compound 13 is {3-[(benzylamino)methyl]-6-nitro-2,3-dihydro-1,4-benzodioxin-5-yl}acetonitrile:

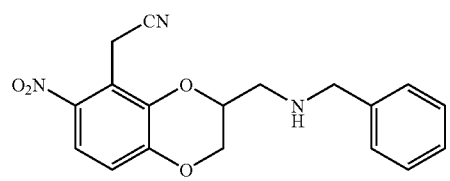 [SMILES: N#CCc1c([N+](=O)[O-])ccc2c1OC(CNCc1ccccc1)CO2]

or a substituted analogue thereof.

In further embodiments, compound 13 is {(3S)-3-[(benzylamino)methyl]-6-nitro-2,3-dihydro-1,4-benzodioxin-5-yl}acetonitrile:

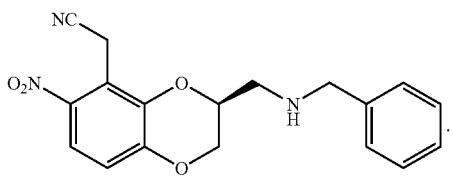

Briefly, as described above, a solution of base such as potassium t-butoxide, NaOH, KOH, sodium t-butoxide, sodium t-pentoxide or potassium t-pentoxide, and a solvent such as DMF is cooled (e.g., to an internal temperature ranging from about 0 to about 5° C.) and then combined with a solution of compound 11 and

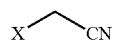

In certain embodiments, the molar equivalents of potassium t-butoxide: compound 11:

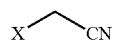

are about 3:1:1.1. After about 1 to about 3 hours, the mixture is acidified (e.g., with HCl to a pH ranging from about 1 to about 2. Subsequent extraction results in the presence of compound 13 in the organic phase, from which it is isolated using standard methods. Certain specific reaction and purification conditions are provided in Example 36. Alternate specific reaction and purification conditions are provided in Example 3M.

Alternatively, as described above, a solution of base such as potassium t-butoxide, NaOH, KOH, sodium t-butoxide, sodium t-pentoxide or potassium t-pentoxide, and a solvent such as DMF is combined with a solution of compound 11 and

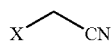

at ambient temperature. In certain embodiments, the molar equivalents of potassium t-butoxide: compound 11:

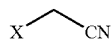

are about 3:1:1.1 to about 4:1:2. After about 1 to about 3 hours, the mixture is acidified (e.g., with HCl to a pH ranging from about 1 to about 2. Subsequent extraction of the byproducts, followed by neutralization of the aqueous phase and extraction, results in the presence of compound 13 in the organic phase, from which it is isolated using standard methods. Certain specific reaction and purification conditions are provided in Example 3H.

In step (14), the nitrile or ester group of compound 13 is hydrolyzed by contact with water or a $C_1$-$C_8$alkanol (e.g., by heating in acidic conditions; typically, the acidic conditions are achieved with $H_2SO_4$, $H_3PO_4$, HCl, or p-TsOH) to yield compound 14 (also referred to herein as a compound of Formula 14). If, however, the $C_1$-$C_8$alkanol is ethanol, then the acid should not be $H_3PO_4$ or p-TsOH. $R_x$ may be hydrogen (i.e., compound 14 is an acid) or $C_1$-$C_8$alkyl, such as methyl or ethyl (i.e., compound 14 is an ester). In certain embodiments, $R_3$ is absent (i.e., n is the integer 0). If R is benzyl and n is the integer 0, then compound 14 is 2-(3-((benzylamino)methyl)-6-nitro-2,3-dihydrobenzo[b][1,4]dioxin-5-yl)acetic acid:

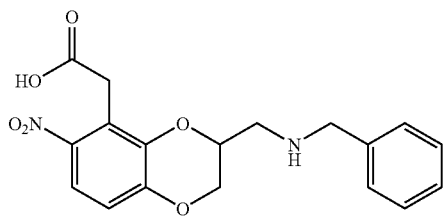 [SMILES: O=C(O)Cc1c([N+](=O)[O-])ccc2c1OC(CNCc1ccccc1)CO2]

or an ester thereof.

Briefly, compound 13 is treated with aqueous acid (eg., HCl or $H_2SO_4$) and heated to between about 80 and about 110° C. for about 4 to about 24 hours. The pH is adjusted to about 8 by addition of aqueous NaOH, extracted into an organic solvent (e.g., $CH_2Cl_2$ or ethyl acetate) and evaporated to a solid residue. Alternatively, compound 13 is dissolved in an alcohol (e.g., MeOH or EtOH) and treated with HCl gas at between about −10 and about 5° C. for about 1 to about 2 hours. The solution is held at about 0° C. for about 1 to about 24 hours then evaporated to a residue. The residue is diluted with an organic solvent such as NMP or DME and washed with dilute aq. HCl. The pH is adjusted to about 10 by addition of NaOH, and extracted into an organic solvent such as MTBE or ethyl acetate. The volatiles are removed giving compound 14 as a syrup. In another alternative ester preparation, compound 13 is dissolved in an alcohol (e.g., MeOH or EtOH), treated with concentrated $H_2SO_4$, and heated to reflux for 1 to 7 days. The solution is diluted with the alcohol used, aqueous $NH_3$ is added until the pH is about 10, and the mixture is stirred for 1 to 18 h. The precipitate is removed by filtration and the volatiles are removed giving compound 14 as a syrup. Within yet another alternative preparation, compound 13 is treated with a mixture of acetic acid and 12 N hydrochloric acid at 100° C. for from 5 to 24 h. Upon cooling, compound 14 is collected by vacuum filtration as the HCl salt ($R_x$=H). Certain specific reaction and purification conditions are provided in Example 3K. Alternate conditions are provided in Example 3I, which illustrates the preparation of compound 14 by heating compound 13 in glacial acetic acid and HCl.

In certain embodiments, compound 14 is (S)-2-(3-((benzylamino)methyl)-6-nitro-2,3-dihydrobenzo[b][1,4]dioxin-5-yl)acetic acid:

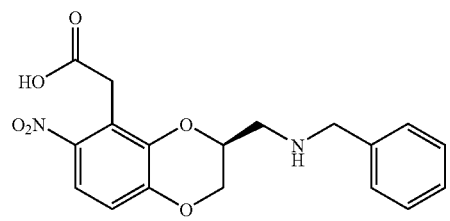 [SMILES: O=C(O)Cc1c([N+](=O)[O-])ccc2c1O[C@@H](CNCc1ccccc1)CO2]

or an ester thereof.

The cyclization in step (15)

is achieved by reducing the nitro group of compound 14 to an amino group and cyclizing, to yield the compound of Formula A. Any of a variety of reducing agents may be employed. If R is benzyl and n is the integer 0, then the compound of Formula A is:

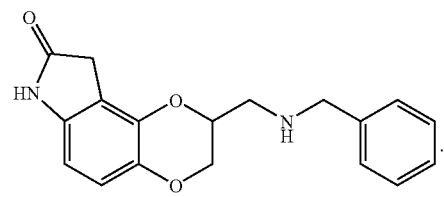 [SMILES: O=C1Cc2c(ccc3c2OC(CNCc2ccccc2)CO3)N1]

Briefly, in certain such reactions, compound 14 is hydrogenated (e.g., under basic conditions) in the presence of reducing agent such as palladium or platinum. In certain embodiments, such hydrogenation is performed under pressure (e.g. about 1.5 to about 50 psig hydrogen) for about 1 to about 72 hours. For example, the hydrogenation can be performed in water with 0.25-1.5 equivalents of NaOH, in methanol with 0-1 equivalent of aqueous NaOH or in methanol with from 1 to 2 equivalents of hydrochloric acid. The solution is then acidified if necessary and heated to a temperature ranging from about 50 to about 80° C. After about 4 to about 24 hours, heating is discontinued and the pH of the solution is adjusted to 9 by addition of aqueous base (e.g., NaOH, Na$_2$CO$_3$, K$_2$CO$_3$). The solution is extracted with an organic solvent such as ethyl acetate and evaporated to a syrup. Certain specific reaction and purification conditions are provided in Example 3L. Alternative hydrogenation conditions, which do not require elevated pressure, are preferred in certain embodiments; representative such conditions are provided in Examples 3J and 3N.

It will be apparent, as indicated by the dotted arrow, that step (14)

may be omitted if W is an ester moiety. In such cases, compound 13 is used directly in step (15).

In certain embodiments, R$_3$ is absent (i.e., n is the integer 0). If R is benzyl, W is COOC$_1$-C$_8$alkyl, and n is the integer 0, then compound 13 is:

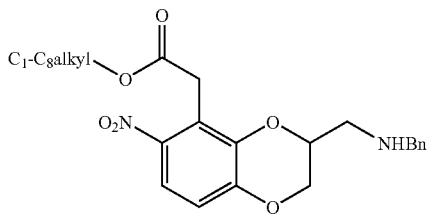

If R is benzyl, W is COOEt, and n is the integer 0, then compound 13 is ethyl-3-[(benzylamino)methyl]-6-nitro-2,3-dihydro-1,4-benzodioxin-5-yl}acetate:

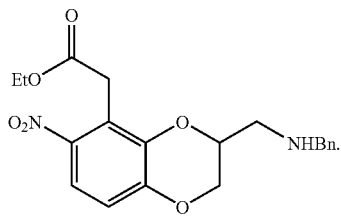

In certain embodiments, compound 13 is ethyl{(3S)-3-[benzylamino)methyl]-6-nitro-2,3-dihydro-1,4-benzodioxin-5-yl}acetate:

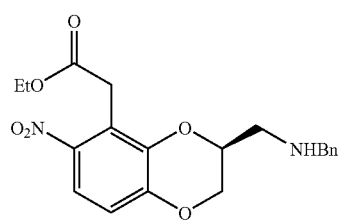

Briefly, in those reactions where W is an ester moiety, compound 13 is hydrogenated in the presence of a reducing agent such as palladium or platinum in a C$_1$-C$_8$alkanol solvent such as ethanol or methanol. Such hydrogenation typically is performed under pressure (e.g., about 15 to about 50 psig hydrogen) for about 1 to about 72 hours. The solution is then acidified (e.g., H$_2$SO$_4$, p-TsOH, HCl, H$_3$PO$_4$) and heated to a temperature ranging from about 40 to about 80° C. After about 4 to about 36 hours, heating is discontinued and the pH of the solution is adjusted to about 10 by addition of aqueous base (e.g., NaOH, Na$_2$CO$_3$, K$_2$CO$_3$). The solution is extracted with an organic solvent such as ethyl acetate or isopropyl acetate and evaporated to a syrup. Alternatively, if W is a carboxylic acid, compound 13 is dissolved in methanol, water or a mixture thereof and hydrogenated in the presence of a reducing agent such as palladium or platinum. The hydrogenation may be performed at atmospheric pressure or at an elevated pressure up to about 50 psig, and for a time ranging from about 15 minutes to 24 hours. The solution is then acidified (e.g., via the addition of H$_2$SO$_4$, p-TsOH, HCl or H$_3$PO$_4$) and heated to a temperature ranging from about 40 to about 60° C. After about 4 to about 36 hours, heating is discontinued, the methanol is removed, and the pH of the solution is adjusted to about 10 by addition of aqueous base (e.g., NaOH, Na$_2$CO$_3$, K$_2$CO$_3$). The solution is extracted with an organic solvent such as ethyl acetate, isopropyl acetate or 2-methyl tetrahydrofuran and evaporated to a syrup.

For Scheme I and Scheme II, it will be apparent that if compound 5 is:

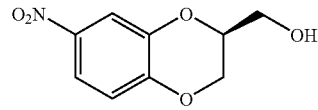 [SMILES: O=[N+]([O-])c1ccc2c(c1)O[C@@H](CO)CO2]

then the subsequent intermediates are also non-racemic, and the resulting substituted aminomethyl-2,3,8,9-tetrahydro-7H-1,4-dioxino[2,3-e]indol-8-one is also non-racemic. In certain embodiments, where R is benzyl, the substituted aminomethyl-2,3,8,9-tetrahydro-7H-1,4-dioxino[2,3-e]indol-8-one prepared by such methods is:

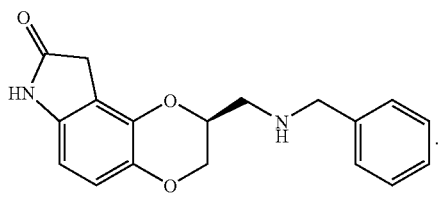 [SMILES: O=C1Cc2c(ccc3c2O[C@@H](CNCc2ccccc2)CO3)N1]

In certain situations, it may be convenient to isolate the substituted aminomethyl-2,3,8,9-tetrahydro-7H-1,4-dioxino[2,3-e]indol-8-one as a salt. Such a salt may be prepared using standard techniques, from any suitable acid such as, for example, acetic, 2-acetoxybenzoic, ascorbic, benzenesulfonic, benzoic, citric, ethane-1,2-disulfonic, formic, fumaric, gentisic, glutaric, glutamic, glycolic, hydrobromic, hydroiodic, hydrochloric, 2-hydroxyethylsulfonic, hydroxymaleic, lactic, maleic, malic, malonic, methanesulfonic, naphthalene-1,5-disulfonic, nicotinic, nitric, pamoic, phenylacetic, phosphoric, propionic, salicylic, stearic, succinic, sulfamic, sulfanilic, sulfuric, tartaric and toluenesulfonic. Also included are the chiral acids such as D-tartaric acid, L-tartaric acid, D-malic acid, L-malic acid, (R)-mandelic acid or (S)-mandelic acid. In general, salt formation involves combining the compound of Formula A with the acid (typically in equimolar amounts and with heating). A precipitate generally forms upon cooling (seed crystals may be added if necessary in order to facilitate the generation of a precipitate). The precipitate may be isolated by filtration. Certain specific reaction and purification conditions are provided in Example 2F.

Other methods for preparing salts of substituted aminomethyl-2,3,8,9-tetrahydro-7H-1,4-dioxino[2,3-e]indol-8-ones are provided in Examples 3N and 3O. The use of hydrochloric acid, methane sulfonic acid or toluenesulfonic acid in the procedure illustrated in Example 3N, is preferred in certain embodiments; phosphoric acid can also be used, but the final product is a syrup. It has been found, in the context of the present invention, that acetic acid does not work well for the reaction described in Example 3N.

The following Examples are offered by way of illustration and not by way of limitation. Unless otherwise specified, all reagents and solvent are of standard commercial grade and are used without further purification. Starting materials are available from commercial suppliers, such as Sigma-Aldrich (St. Louis, Mo.), or are synthesized using procedures that are known in the art.

EXAMPLES

Certain abbreviations used in the following Examples and elsewhere herein include:
Ac Acetyl
aq Aqueous
Bn Benzyl
br broad (NMR)
d doublet (NMR)
DMF dimethylformamide
DMSO dimethylsulfoxide
ee enantiomeric excess
eq equivalent(s)
EtOH Ethanol
h hour(s)
HMDS hexamethyldisilazane
IPA or i-PrOH 2-propanol, isopropanol
LCMS liquid chromatography-mass spectrometry
MHz Megahertz
min minute(s)
MTBE methyl tert-butyl ether
NMP N-methylpyrrolidone
NMR nuclear magnetic resonance
pyr Pyridine
rt room temperature
s singlet (NMR)
t triplet (NMR)
TBAB tetrabutylammonium bromide
THF tetrahydrofuran
TLC thin-layer chromatography
Ts p-toluenesulfonyl
UV Ultraviolet

NMR $^1$H NMR data is obtained on either a Varian 300 (300 MHz) Mercury Plus or Varian 400 (400 MHz) Mercury Plus spectrometer as noted.

Analytical LC/MS

Mass spectroscopy in the following Examples is Electrospray MS, obtained in positive ion mode using a Waters ZMD II Mass Spectrometer (Waters Corp.; Milford, Mass.), equipped with a Waters 600 series pump (Waters Corp.), a Waters 996 photodiode array detector (Waters Corp.), and a Gilson 215 autosampler (Gilson, Inc.; Middleton, Wis.). MassLynx™ (Waters Corp.; Milford, Mass.) version 4.0 software with OpenLynx processing is used for data collection and analysis. MS conditions are: capillary voltage=3.5 kV; cone voltage=30 V, desolvation and source temperature=250° C. and 100° C., respectively; mass range=100-750 with a scan time of 0.75 seconds and an interscan delay of 0.15 seconds. LCMS conditions are:

| | |
|---|---|
| Column | 4.6 × 30 mm, XTerra MS C18, 5 µm or equivalent |
| UV | 10 spectra/sec; 210 to 350 nm scan range |
| Extracted Wavelengths | 220 and 254 nm |
| Flow rate | 4.0 mL/min |
| Injection Volume | 2-20 µl |
| Analysis Time | 4 min |

Standard Method:

| | |
|---|---|
| Mobile phase A | 95% Water, 5% Methanol with 0.05% Formic acid |
| Mobile phase B | 95% Methanol, 5% Water with 0.025% Formic acid |

Gradient:

| Time (min) | % B |
|---|---|
| 0 | 5 |
| 0.01 | 5 |
| 2.0 | 100 |
| 3.50 | 100 |
| 3.51 | 5 |

Basic Method:

| | |
|---|---|
| Mobile phase A: | 95% Aqueous 10 mM Ammonium Formate, 5% Methanol |
| Mobile phase B: | 95% Methanol, 5% Water with 0.025% Formic acid |

Gradient:

| Time (min) | % B |
|---|---|
| 0 | 10 |
| 0.01 | 10 |
| 2.0 | 100 |
| 3.50 | 100 |
| 3.51 | 10 |

Example 1

Preparation of Intermediates

This Example illustrates the synthesis of representative intermediates useful in the preparation of substituted aminomethyl-2,3,8,9-tetrahydro-7H-1,4-dioxino[2,3-e]indol-8-ones.

A. Preparation of 2-(benzyloxy)-1-methoxy-4-nitrobenzene

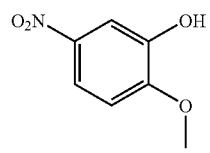

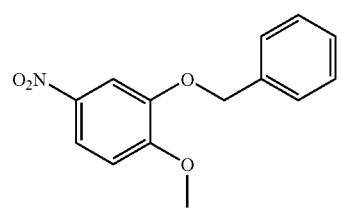

Method 1: A 500 mL, 3-necked Morton flask equipped with a thermocouple and nitrogen inlet is charged with 2-methoxy-5-nitrophenol (20.00 g, 118.3 mmol) and DMF (80 mL). Solid potassium carbonate (19.60 g, 141.8 mmol) is added in one portion. Benzyl chloride (14.30 mL, 124.0 mmol) is added and the flask is immersed in an oil bath. The oil is heated to 70° C. for 18 h, and then the solution is allowed to cool to rt. Water (160 mL) is added to the reaction mixture, resulting in the formation of a precipitate. The suspension is stirred for 1 h, and then the precipitate is collected by vacuum filtration. The filter cake is washed with water (50 mL) and suction dried giving 30.31 g (99%) of the title compound as a tan powder.

Method 2: 2-Methoxy-5-nitrophenol (244 g, 1.44 mol) is placed in a flask (5 L) under nitrogen at rt. Toluene (2.0 L) is added, followed by benzyl bromide (258.6 g, 1.51 moles), TBAB (12.3 g) and NaOH (20% in water, 1.0 L) to give a red suspension. The reaction mixture is slowly heated to 50-55° C. After 1 h, the mixture converts from suspension to a two phase solution. The reaction is complete in 3 h. The reaction mixture is cooled to 25° C., and the two phases are separated. The organic phase is washed once with NaOH (2.5 N, 300 mL) and then evaporated directly to give 372.5 g (100%) of the title compound as a yellow solid.

LCMS (Standard Method): 2.81 min, 260 (M+H)$^+$. $^1$H NMR (300 MHz, CDCl$_3$) δ 7.87 (dd, J=2.5, 8.8 Hz, 1H), 7.64 (d, J=2.5 Hz, 1H), 7.48-7.34 (m, 5H), 6.92 (d, J=9.1 Hz, 1H), 5.20 (s, 2H), 3.98 (s, 3H).

B. Preparation of 2-(benzyloxy)-4-nitrophenol

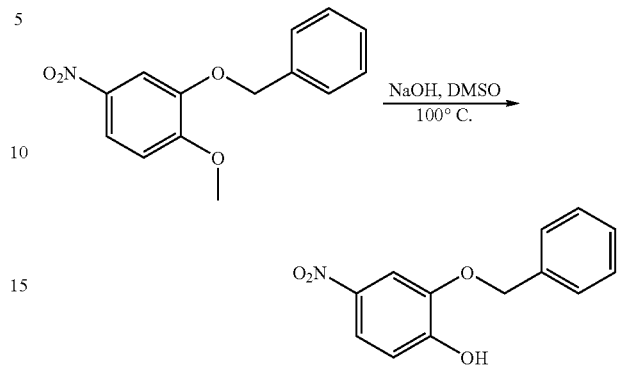

A 200 mL round bottomed flask is charged with 2-(benzyloxy)-1-methoxy-4-nitrobenzene (10.00 g, 38.6 mmol) and DMSO (30 mL). To the stirred suspension is added NaOH (10 N, 10 mL, 100 mmol), and the mixture is heated to 100° C. for 5 h. The solution is cooled to rt, and immersed in a water ice bath, and water (30 mL) is added to the solution. The pH is adjusted to ~1 by addition of concentrated HCl (10 mL, 121 mmol). The solution is extracted once with toluene (80 mL). The organic phase is washed successively with water (20 mL) and brine (20 mL), and evaporated to dryness yielding 9.37 g (99%) of the title compound as a yellow solid. LCMS (Standard Method): 2.70 min, 268 (M+Na)$^+$. $^1$NMR (300 MHz, CDCl$_3$) δ 7.92-7.86 (m, 2H), 7.45-7.41 (m, 5H), 7.00 (d, J=8.8 Hz, 1H), 5.20 (s, 2H).

C. Preparation of (2R)-2-{[2-(benzyloxy)-4-nitrophenoxy]methyl}oxirane

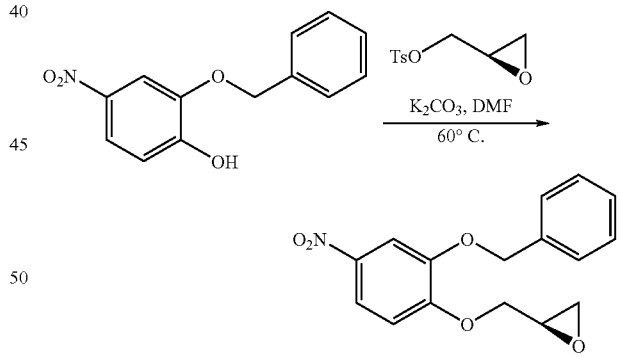

A 500 mL round bottomed flask equipped with a nitrogen inlet and a magnetic stir bar is charged with: 2-(benzyloxy)-4-nitrophenol (10.00 g, 40.8 mmol), potassium carbonate (7.05 g, 51.0 mmol), (R)-(−)-glycidyl tosylate (10.00 g, 43.8 mmol) and DMF (65 mL). The mixture is immersed in an oil bath heated to 60° C. and stirred for 18 h. The solution is allowed to cool to rt, then water (200 mL) is slowly added. The resulting suspension is stirred for 2 h, the precipitate is collected by vacuum filtration and the filter cake is washed with water (25 mL). The cake is dried under suction to yield 10.70 g (87%) of the title compound as a light yellow powder. LCMS (Standard Method): 2.74 min, 302 (M+H)$^+$. $^1$H NMR (300 MHz, CDCl$_3$) δ 7.89 (dd, J=2.6, 9.0 Hz, 1H), 7.81 (d, J=2.6 Hz, 1H), 7.48-7.34 (m, 5H), 6.98 (d, J=8.8 Hz, 1H), 5.19 (s, 2H), 4.43 (dd, J=2.7, 11.5 Hz, 1H), 4.08 (dd, J=5.8, 11.5 Hz, 1H), 3.43-3.39 (m, 1H), 2.95-2.91 (m, 1H), 2.81-2.78 (m, 1H).

D. Alternate Preparation of (2R)-2-{[2-(benzyloxy)-4-nitrophenoxy]methyl}oxirane

Step 1. Preparation of potassium 2-(benzyloxy)-4-nitrophenolate

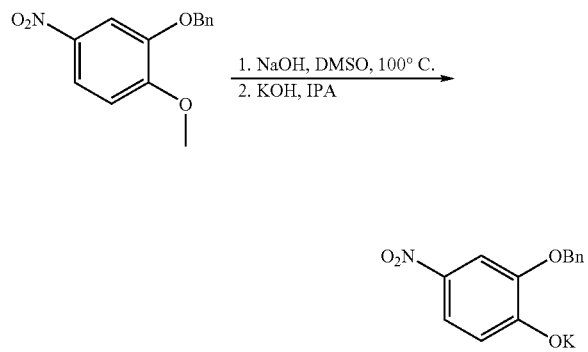

A 22 L flask equipped with a mechanical stirrer, thermocouple and heating mantel is charged with 2-(benzyloxy)-1-methoxy-4-nitrobenzene (1.46 kg, 5.66 mol) and DMSO (4.5 L). To the stirred suspension is added aqueous 10 N NaOH (1.5 L, 15.0 mol) and the resulting mixture is heated to achieve an internal temperature of 95° C. Heating is continued for 15 h, and then the solution is cooled to 20° C. The solution is transferred to a 30 L jacketed reactor, aqueous 3 N HCl (4 L) is added to adjust the pH to 8.5, and then toluene (11 L) is added and the mixture is rapidly stirred. Aqueous 3 N HCl is added until pH 1 is obtained (1.7 L), stirring is stopped, the layers are allowed to separate and the aqueous phase is removed. Water (2.5 L) is added, the mixture is rapidly stirred for 15 min, the layers are allowed to separate and the aqueous layer is removed. The reactor is then equipped with a distillation head, a reflux condenser and a vacuum line. The vacuum is turned on and the jacket temperature is set to 80° C. The distillation is continued until 6.5 L of distillate is removed. The concentrated solution is cooled to 20° C. and held in bottles.

A 30 L jacketed reactor is charged with isopropanol (11.3 L) and potassium hydroxide (317.6 g, 5.66 mol) The mixture is heated to 40° C. to obtain a slightly cloudy solution. The toluene solution from above is added to the warm isopropanol solution over a 1.5 h period. The stirred suspension is cooled to 20° C., held to 2 h and collected by vacuum filtration. The filter cake is washed with isopropanol (1 L) and suction dried to give the title compound (1.31 kg, 82%) as an orange powder. LCMS (Standard Method): 2.70 min, 268 (M+Na)+. 1H NMR (300 MHz, DMSO-d6) δ 7.59 (dd, J=2.9, 9.2 Hz, 1H), 7.42-7.28 (m, 6H), 5.93 (d, J=9.5 Hz, 1H), 4.94 (s, 2H).

Step 2. Preparation of (2R)-2-{[2-(benzyloxy)-4-nitrophenoxy]methyl}oxirane

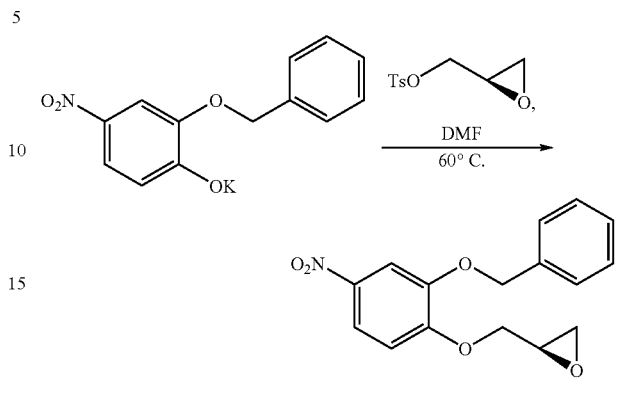

A 30 L jacketed reactor is charged with potassium 2-(benzyloxy)-4-nitrophenolate (1.31 kg, 4.62 mol), (R)-glycidyl tosylate (1.13 kg, 4.96 mol) and DMF (6.5 L). The resulting suspension is heated until an internal temperature of 65° C. is obtained, and is then stirred for 18 h. The solution is cooled to 20° C., and then water (2 L) is added over 30 min. The solution is seeded with 2 g of the desired product, and the addition of water is resumed (9 L over 1.25 h). The slurry is stirred for 2.5 h, and then collected by vacuum filtration. The reactor and filter cake are washed with water (5 L total) and suction dried to give the title compound (1370 g, 98%) as an off-white powder. LCMS (Standard Method): 2.74 min, 302 (M+H)+. 1H NMR (300 MHz, CDCl3) δ 7.89 (dd, J=2.6, 9.0 Hz, 1H), 7.81 (d, J=2.6 Hz, 1H), 7.48-7.34 (m, 5H), 6.98 (d, J=8.8 Hz, 1H), 5.19 (s, 2H), 4.43 (dd, J=2.7, 11.5 Hz, 1H), 4.08 (dd, J=5.8, 11.5 Hz, 1H), 3.43-3.39 (m, 1H), 2.95-2.91 (m, 1H), 2.81-2.78 (m, 1H).

E. Preparation of [(2S)-7-nitro-2,3-dihydro-1,4-benzodioxin-2-yl]methanol

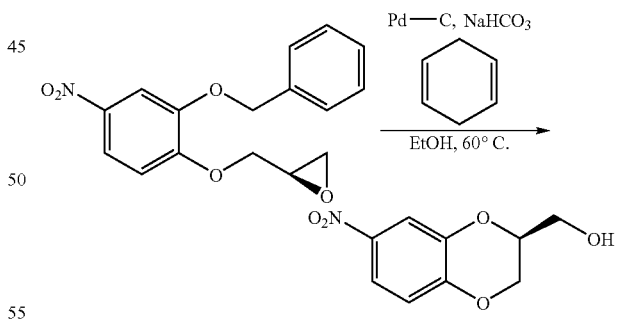

A 3 L 3-necked flask equipped with a mechanical stirrer, a reflux condenser, a thermocouple and a heating mantel is charged with EtOH (1500 mL), (2R)-2-{[2-(benzyloxy)-4-nitrophenoxy]methyl}oxirane (70.00 g, 0.232 mol), sodium bicarbonate (38.98 g, 0.464 mol) and 1,4-cyclohexadiene (39.56 mL, 0.418 mol). Argon gas is bubbled through the suspension for 5 min, and then the bubbling is discontinued, and palladium (10% on carbon, 4.9 g) is added. The mixture is heated to an internal temperature of 60° C. and stirred at 60° C. for 1 h. The solution is cooled to rt, filtered through a pad of celite and evaporated to dryness. The residue is dissolved in EtOAc (800 mL), and washed with 1 N HCl (2×100 mL) and brine (100 mL), and the volatiles are removed. The title compound (47.33 g, 93%) is obtained as a tan powder. LCMS (Standard Method): 2.23 min, 212 (M+H)+. 1NMR (300 MHz, CDCl3) δ 7.81-7.76 (m, 2H), 6.96 (d, J=8.5 Hz, 1H), 4.42 (dd, J=2.1, 11.2 Hz, 1H), 4.32-4.18 (m, 2H), 3.98-3.85 (m, 2H), 2.03 (br s, 1H).

F. Alternative Preparation of [(2S)-7-nitro-2,3-dihydro-1,4-benzodioxin-2-yl]methanol

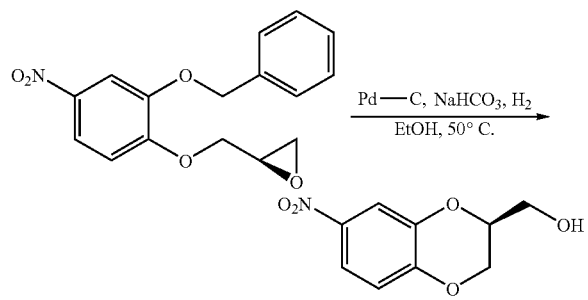

A 5 L four necked flask equipped with a heating mantle, mechanical stirrer, thermocouple, gas inlet adapter and gas outlet adapter is charged with (2R)-2-{[2-(benzyloxy)-4-nitrophenoxy]methyl}oxirane (100.00 g, 0.33 mol), sodium bicarbonate (27.88 g, 0.33 mol), palladium (5% on carbon, 50% water, 15 g) and ethanol (2 L). The mixture is heated to 50° C. The stirring is stopped and the flask is flushed with hydrogen gas (3 L). Stirring is resumed and hydrogen gas is titrated into the solution [7.4 L (0.33 mol) over 130 min]. Heating is discontinued and nitrogen is bubbled through the solution for 20 min. Once the solution is cooled to 25° C., the mixture is filtered through a pad of celite and the filter cake is washed with ethanol (1 L). The resulting solution is concentrated by rotary evaporation removing 2.5 L of ethanol. The solution is transferred to a 5 L four necked flask equipped with a mechanical stirrer, thermocouple and an addition funnel. Water (750 mL) is slowly added to the stirred solution over 30 min, and the solution is stirred for 15 min at which point a precipitate forms. Additional water (1.5 L) is added over 60 min and the suspension is stirred for 48 h. The precipitate is collected by vacuum filtration, and then the filter cake is washed with water and suction dried. The title compound (49.01 g, 70%) is obtained as a tan powder. LCMS (Standard Method): 2.23 min, 212 (M+H)+. 1NMR (300 MHz, CDCl3) δ 7.81-7.76 (m, 2H), 6.96 (d, J=8.5 Hz, 1H), 4.42 (dd, J=2.1, 11.2 Hz, 1H), 4.32-4.18 (m, 2H), 3.98-3.85 (m, 2H), 2.03 (br s, 1H).

G. Alternative Preparation of [(2S)-7-nitro-2,3-dihydro-1,4-benzodioxin-2-yl]methanol

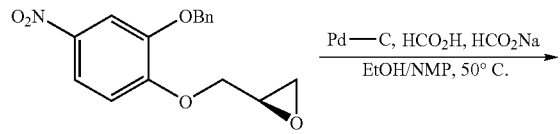

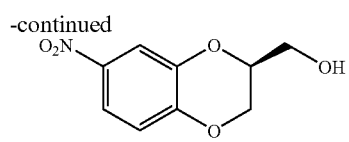

A 1 L three necked flask equipped with a mechanical stirrer, thermocouple and heating mantle is charged with (2R)-2-{[2-(benzyloxy)-4-nitrophenoxy]methyl}oxirane (50.00 g, 0.17 mol), ethanol (400 mL) N-methyl-2-pyrrolidone (100 mL) and palladium (5% on carbon, 50% water, 7.5 g). The mixture is heated to an internal temperature of 45° C., at which point a solution of sodium formate (1.40 g, 0.022 mol) in 95% formic acid (8.40 mL, 0.208 mol) is added over 5 min. The reaction is monitored by LCMS, and no starting material remained after 4 h. The pH of the reaction mixture is found to be about 2. 1 N NaOH (16 mL, 16 mmol) is added to achieve a pH of 9. Heating is discontinued, and the solution is allowed to cool to room temperature overnight. The catalyst is removed by filtration through celite, and the ethanol is removed by rotary evaporation. The flask containing the product in NMP is equipped with a magnetic stirrer and an addition funnel. Water (150 mL) is added via addition funnel over 15 min, followed by seed crystals, and the resulting suspension is stirred for 15 min. Additional water (250 mL) is added over 30 min, during which time more precipitate forms. The suspension is stirred for 2 h and the solid is collected by vacuum filtration. The filter cake is washed with water (200 mL) and suction dried under nitrogen. The title compound is obtained as a red/brown solid (24.54 g, 70%, 94% ee); m.p. 110° C. LCMS (Basic Method): 2.13 min, 212 (M+H)+. 1H NMR (300 MHz, CDCl3) δ 7.81-7.76 (m, 2H), 6.96 (d, J=8.5 Hz, 1H), 4.42 (dd, J=2.1, 11.2 Hz, 1H), 4.32-4.18 (m, 2H), 3.98-3.85 (m, 2H), 2.03 (br s, 1H).

H. Alternative Preparation of [(2S)-7-nitro-2,3-dihydro-1,4-benzodioxin-2-yl]ethanol

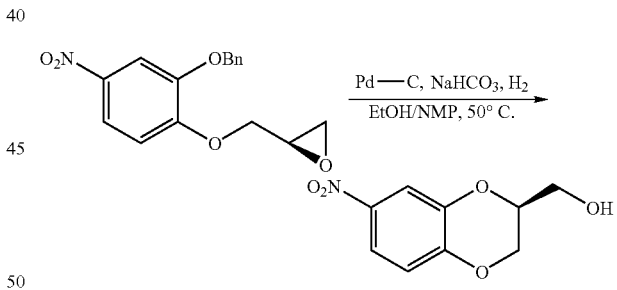

A 500 mL three necked Morton flask equipped with magnetic stir bar, thermocouple, gas inlet adapter and gas outlet adapter is charged with (2R)-2-{[2-(benzyloxy)-4-nitrophenoxy]methyl}oxirane (20.00 g, 66.4 mmol), sodium bicarbonate (5.58 g, 66.4 mmol), palladium (5% on carbon, 50% water, 3 g), ethanol (136 mL) and NMP (24 mL). The flask is immersed in an oil bath and heated to 50-52° C. (internal) to effect solution. The stirring is stopped and the flask is flushed with hydrogen gas (300 mL). Stirring is resumed and hydrogen gas is titrated into the solution [1550 mL (69.2 mmol) over 5.5 h]. Heating is discontinued, and a flow of nitrogen is used to sweep the head space for 20 min. Once the solution is cooled to 25° C., the mixture is filtered through a pad of celite and the filter cake is washed with ethanol (50 mL). The resulting solution is concentrated by rotary evaporation removing ~200 mL of ethanol. The solution is transferred to a separatory funnel and i-PrOAc (220 mL) is added followed by water (200 mL). The mixture is thoroughly shaken and the bottom aqueous layer is drained and discarded. The product containing organic layer is washed with water (3×50 mL), and transferred to a 500 mL three necked flask equipped with a magnetic stir bar, thermocouple, heating mantel, and a distillation head. The i-PrOAc is removed by distillation at atmospheric pressure. Once ~180 mL has been collected, pyridine (80 mL) is added and the distillation is continued until the head temperature is 108° C. The solution is allowed to cool to room temperature and used directly as illustrated in Schemes I and II, and as described in the Examples below.

Example 2

Preparation of Substituted Aminomethyl-2,3,8,9-tertrahydro-7H-1,4-dioxino[2,3-e]indol-8-ones This Example illustrates the synthesis of representative substituted aminomethyl-2,3,8,9-tetrahydro-7H-1,4-dioxino [2,3-e]indol-8-ones via the route illustrated in Scheme I.

A. Preparation of [(3S)-3-(hydroxymethyl)-6-nitro-2,3-dihydro-1,4-benzodioxin-5-yl]acetonitrile

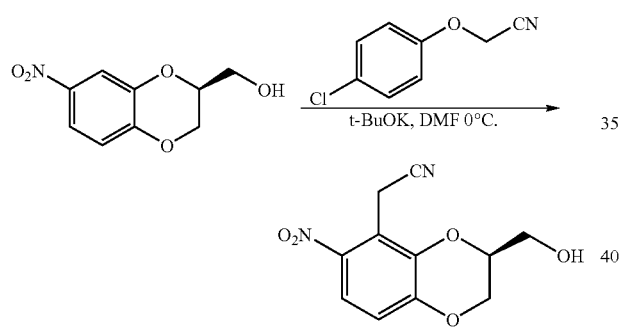

A 5 L 3-necked flask equipped with a mechanical stirrer is charged with solid potassium t-butoxide (103.00 g, 0.918 mol) and DMF (1900 mL). The stirred solution is cooled until the internal temperature is 0° C., and a DMF (1100 mL) solution containing [(2S)-7-nitro-2,3-dihydro-1,4-benzo-dioxin-2-yl]methanol (47.33 g, 0.224 mol) and (4-chlorophe-noxy)acetonitrile (39.05 g, 0.233 mol) is added over 45 min. The reaction is quenched with 1 N HCl (1 L) and the volatiles are removed by rotary evaporation (~3 L removed). The residue is dissolved in water (2 L) and extracted with EtOAc (3×600 mL). The combined extracts are washed with water (2×300 mL), 1 N NaOH (3×400 mL) and brine (300 mL), and evaporated to give an orange/brown solid. The solid is suspended with stirring in MTBE (300 mL) for 30 min. The solid is collected by vacuum filtration, washed with MTBE (50 mL) and then suction dried giving the title compound (33.60 g, 60%) as a tan solid. LCMS (Standard Method): 2.14 min, 251 (M+H)⁺. ¹H NMR (300 MHz, CDCl₂) δ 7.77 (d, J=9.2 Hz, 1H), 7.00 (d, J=9.2 Hz, 1H), 4.48-4.37 (m, 2H). 4.28-3.91 (series of m, 5H), 2.32 (br s, 1H).

B. Preparation of [(3S)-3-(hydroxymethyl)-6-nitro-2,3-dihydro-1,4-benzodioxin-5-yl]acetic acid

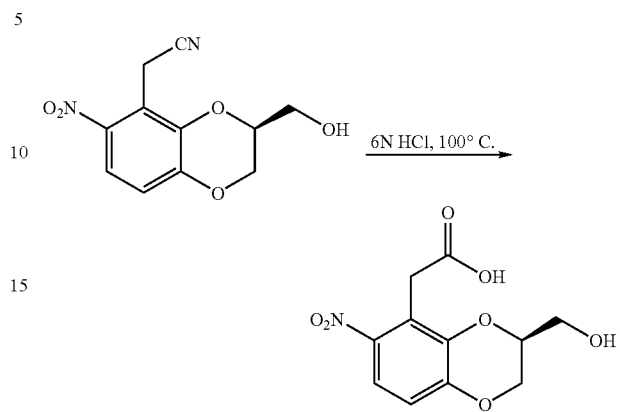

A 500 mL flask is charged with [(3S)-3-(hydroxymethyl)-6-nitro-2,3-dihydro-1,4-benzodioxin-5-yl]acetonitrile (31.00 g, 0.124 mol) and hydrochloric acid (6 N, 250 mL, 1.5 mol). The suspension is heated to 110° C. for 5 h, at which point heating is discontinued. The mixture is stirred for 16 h, and the resulting solid is collected by vacuum filtration. The filter cake is washed sequentially with water (20 mL) and MTBE (20 mL), giving the title compound (25.09 g, 75%) as a brown powder. LCMS (Standard Method): 2.09 min, 292 (M+Na)⁺. ¹H NMR (300 MHz, DMSO-d6) δ 7.66 (d, J=9.2 Hz, 1H), 7.01 (d, J=9.2 Hz, 1H), 5.13 (br s, 1H), 4.43 (dd, J=2.3, 11.3 Hz, 1H), 4.25-4.18 (m, 1H), 4.10 (dd, J=7.4, 11.3 Hz, 1H), 3.94 (s, 2H), 3.64 (d, J=5.2 Hz, 2H), OH not observed.

C. Preparation of (2S)-2-(hydroxymethyl)-2,3,8,9-tetrahydro-7H-[1,4]dioxino[2,3-e]indol-8-one hydrate

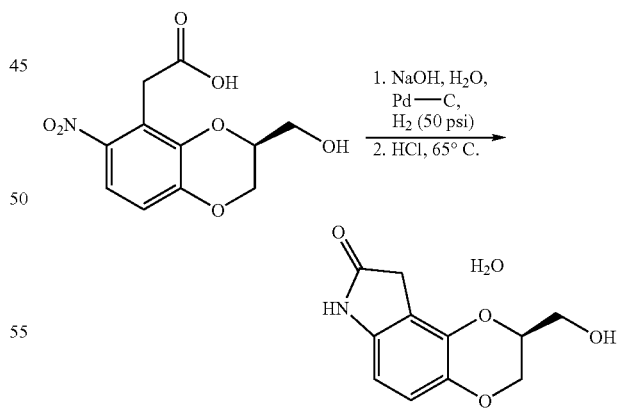

A Parr hydrogenation shake flask is charged with [(3S)-3-(hydroxymethyl)-6-nitro-2,3-dihydro-1,4-benzodioxin-5-yl] acetic acid (20.00 g, 74.2 mmol), NaOH (0.33 N, 300 mL, 99 mmol) and palladium (10% on carbon, 1.6 g). The vessel is pressurized to 50 psi with hydrogen and shaken for 3 h, at which point the pressure is released and the mixture is filtered through celite. The solution is acidified with concentrated. HCl (20 mL) and heated to 65° C. for 7 h. The heating is discontinued, and the suspension is stirred overnight. The precipitate is collected by vacuum filtration, and the filter cake is washed with water (50 mL) and dried under suction to give the title compound (13.81 g, 84%) as a tan powder. LCMS (Standard Method): 1.81 min, 222 (M+H)+. ¹NMR (300 MHz, DMSO-d6) δ 10.17 (br s, 1H), 6.66 (d, J=8.2 Hz, 1H), 6.27 (d, J=8.2, 1H), 5.03 (br s, 1H), 4.25-4.13 (m, 2H), 3.98-3.91 (m, 1H), 3.65-3.57 (m, 2H), 3.31 (br s, 4H).

D. Preparation of [(2R)-8-oxo-2,3,8,9-tetrahydro-7H-[1,4]dioxino[2,3-e]indol-2-yl]methyl 4-methylbenzenesulfonate

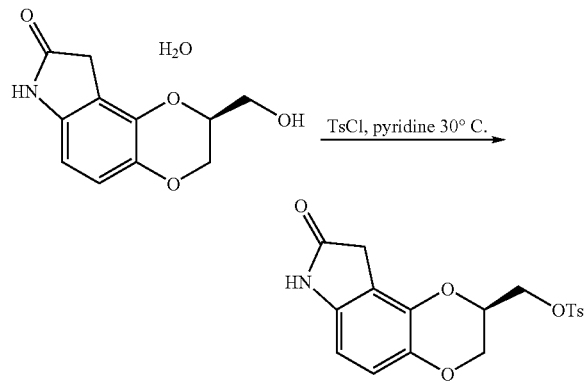

A 200 mL flask is charged with (2S)-2-(hydroxymethyl)-2,3,8,9-tetrahydro-7H-[1,4]dioxino[2,3-e]indol-8-one hydrate (9.37 g, 39.2 mmol) and pyridine (60 mL). The pyridine is removed by rotary evaporation to give (2S)-2-(hydroxymethyl)-2,3,8,9-tetrahydro-7H-[1,4]dioxino[2,3-e]indol-8-one as a brown paste. The residue is dissolved in fresh pyridine (60 mL), the solution is heated to 30° C., and p-toluenesulfonyl chloride (11.20 g, 58.8 mmol) in toluene (23.5 mL) is added over 30 min. The solution is stirred for 8 h, and then isopropanol (100 mL) is added. The resulting suspension is cooled to 5° C. and the precipitate is collected by vacuum filtration. The filter cake is washed with isopropanol (20 mL) and suction dried to give the title compound (7.81 g, 53%) as a yellow powder. LCMS (Standard Method): 2.50 min, 376 (M+H)+. ¹H NMR (300 MHz, DMSO-d6) δ 10.19 (br s, 1H), 7.76 (d, J=8.1 Hz, 2H), 7.41 (d, J=8.1 Hz, 2H), 6.63 (d, J=8.2 Hz, 1H), 6.27 (d, J=8.2 Hz, H), 4.51-4.46 (m, 1H), 4.32 (dd, J=3.0, 11.3 Hz, 1H), 4.20-4.14 (m, 2H), 3.96 (dd, J=5.9, 11.6 Hz, 1H), 3.13 (ABq, 2H, J=22.3 Hz, Δv=42.4 Hz), 2.38 (s, 3H).

E. Preparation of (2S)-2-[(benzylamino)methyl]-2,3,8,9-tetrahydro-7H-[1,4]dioxino[2,3-e]indol-8-one

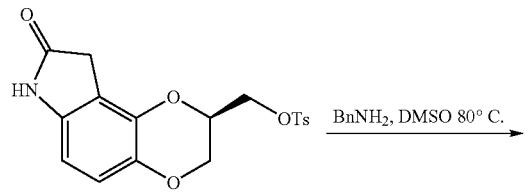

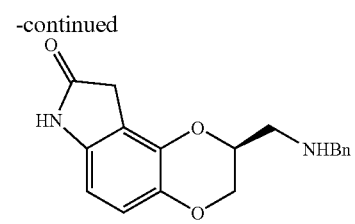

A 25 mL, flask is charged with [(2R)-8-oxo-2,3,8,9-tetrahydro-7H-[1,4]dioxino[2,3-e]indol-2-yl]methyl 4-methylbenzenesulfonate (1.00 g, 2.7 mmol) and DMSO (8.0 mL). Nitrogen gas is bubbled through the solution for 10 min, benzylamine (0.73 mL, 6.7 mmol) is added and nitrogen is bubbled through the mixture for another 15 min. The flask is immersed in an 85° C. oil bath and stirred for 18 h. The solution is cooled, water (24 mL) is added and the resulting solution is extracted with MTBE (3×15 mL). The combined organic extracts are washed successively with water (10 mL), saturated NH₄Cl (10 mL) and saturated NaHCO₃ (10 mL), and are evaporated to give the crude title compound (0.85 g, 101%) as a red syrup. LCMS (Basic Method): 1.84 min, 311 (M+H)+. ¹H NMR (400 MHz, CDCl₃) δ 10.4 (br s, 1H), 7.35-7.27 (m, 5H), 6.73 (d, J=8.3 Hz, 1H), 6.36 (d, J=8.3 Hz, 1H), 4.37-4.35 (m, 1H), 4.25 (dd, J=2.2, 11.5 Hz, 1H), 4.03 (dd, J=7.3, 11.5 Hz, 1H), 3.88 (s, 2H), 3.44 (s, 2H), 2.97-2.88 (m, 2H), 8.9 (br s, 1H).

F. Preparation of (2S)-2-[(benzylamino)methyl]-2,3,8,9-tetrahydro-7H-[1,4]dioxino[2,3-e]indol-8-one (2E)-but-2-enedioate

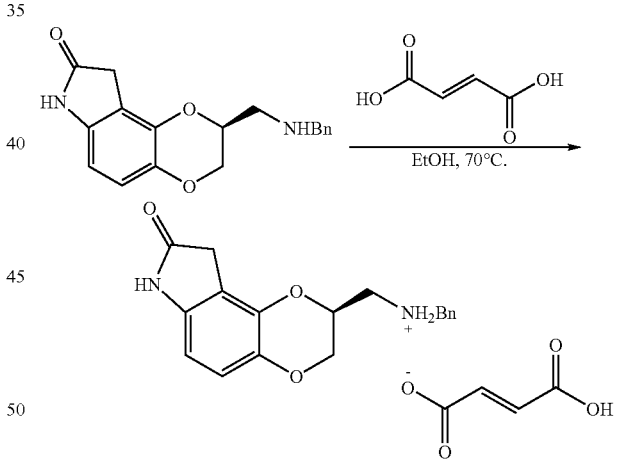

Crude (2S)-2-[(benzylamino)methyl]-2,3,8,9-tetrahydro-7H-[1,4]dioxino[2,3-e]indol-8-one (0.85 g, 2.7 mmol) is dissolved in EtOH (18 mL) and heated to 70° C. Solid fumaric acid (0.31 g, 2.7 mmol) is added in one portion to the hot solution, and the heat is turned off. Once the solution is at 55° C., seed crystals are introduced and the mixture is allowed to continue cooling to rt over 1.5 h. The slurry is further cooled to 5° C. by immersion in an ice water bath held at this temperature for 30 min and collected by vacuum filtration. The filter cake is washed with cold EtOH (10 mL) and dried under suction giving the title compound (0.70 g, 62%) as a pink powder. LCMS (Basic Method): 1.84 min, 311 (M+H)+. ¹H NMR (300 MHz, DMSO-d6) δ 10.17 s, 1H), 7.38-7.21 (m, 5H), 6.66 (d, J=8.2 Hz, 1H), 6.57 (s, 2H), 6.28 (d, J=8.2 Hz, 1H), 4.35-4.33 (m, 1H), 4.25 (dd, J=2.2, 11.7 Hz, 1H), 3.96 (dd, J=6.4, 11.5 Hz, 1H), 3.83 (s, 2H), 3.32 (s, 2H), 2.83-2.81 (m, 2H), NH, and two OH's not observed.

Example 3

Preparation of Representative Intermediates

This Example illustrates the synthesis of representative intermediates useful in the synthesis of substituted aminomethyl-2,3,8,9-tetrahydro-7H-1,4-dioxino[2,3-e]indol-8-ones via the route illustrated in Scheme II.

A. Preparation of [7-nitro-2,3-dihydro-1,4-benzodioxin-2-yl]methyl 4-methylbenzenesulfonate

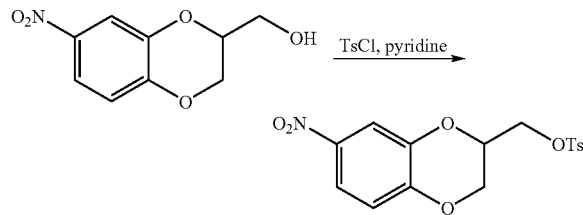

A 500 mL round bottomed flask equipped with a magnetic stir bar is charged with [7-nitro-2,3-dihydro-1,4-benzodioxin-2-yl]methanol (37.3 g, 177 mmol) and anhydrous pyridine (150 mL). The solution is cooled to 5° C. and p-toluenesulfonyl chloride (42.1 g, 221 mmol) is added in one portion. After 1 h, the cooling bath is removed, and the solution is stirred for another 3 h. The reaction mixture is poured into a rapidly stirred flack containing water (750 mL). The precipitate is collected by vacuum filtration, and the filter cake is rinsed with water and suction dried to give the title compound (63.8 g, 99%) as yellow granules. LCMS (Standard Method): 2.81 min, 388 (M+Na)$^+$. $^1$H NMR (300 MHz, DMSO-d6) δ7.79-7.72 (m, 3H), 7.49-7.42 (m, 3H), 7.06 (d, J=8.8 Hz, 1H), 4.59-4.55 (m, 1H), 4.41 (dd, J=2.6, 11.6 Hz, 2H), 4.22 (dd, J=6.3, 11.5 Hz, 1H), 4.12 (dd, J=6.8, 11.7 Hz, 1H), 2.38 (s, 3H).

B. Preparation of [(2R)-7-nitro-2,3-dihydro-1,4-benzodioxin-2-yl]methyl 4-methylbenzenesulfonate

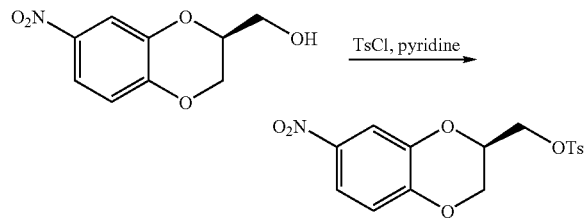

A 5 L three necked flask equipped with a mechanical stirrer and thermocouple is changed with [(2S)-7-nitro-2,3-dihydro-1,4-benzodioxin-2-yl]methanol (210.4 g, 0.996 mol) and anhydrous pyridine (600 mL). The flask is immersed in an ice/brine bath to achieve an internal temperature of 0-1° C. To this is added a solution of p-toluenesulfonyl chloride (220.0 g, 1.15 mol) is dissolved in pyridine (200 mL) over 30 min. The bath is allowed to expire, and the mixture is stirred for 18 h at room temperature. Water (1600 mL) is added at a constant rate over 45 min. The resulting suspension is stirred for 1 h, and then the precipitate is collected by vacuum filtration onto a medium porosity fritted funnel. The filter cake is washed with water (1600 mL) and suction dried under nitrogen to give [(2R)-7-nitro-2,3-dihydro-1,4-benzodioxin-2-yl]methyl 4-methylbenzenesulfonate (356.8 g, 98%) as a tan powder; m.p. 138° C. LCMS (Standard Method): 2.78 min, 388 (M+Na)$^+$. $^1$H NMR (300 MHz, DMSO-d6) δ7.79-7.72 (m, 3H), 7.49-7.42 (m,3H), 7.06 (d, J=8.8 Hz, 1H), 4.59-4.55 (m, 1H), 4.41 (dd, J=2.6, 11.6 Hz, 2H), 4.22 (dd, J=6.3, 11.5 Hz, 1H), 4.12 (dd, J=6.8, 11.7 Hz, 1H), 2.38 (s, 3H).

C. Preparation of [(2R)-7-nitro-2,3-dihydro-1,4-benzodioxin-2-yl]methyl 4-methylbenzenesulfonate

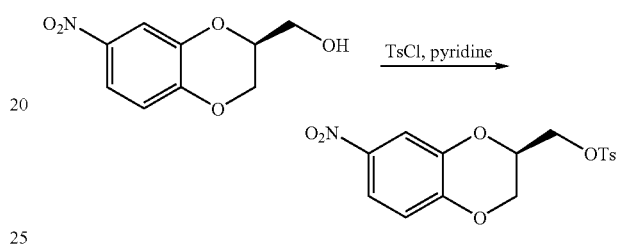

A 500 mL three necked flask equipped with a magnetic stir bar and thermocouple and the pyridine solution of [(2S)-7-nitro-2,3-dihydro-1,4-benzodioxin-2-yl]methanol (~66.4 mmol) from Example 1H is immersed in an ice/brine bath to achieve an internal temperature of 0-1° C. p-toluenesulfonyl chloride (14.55 g, 76.3 mmol) is dissolved in pyridine (17 mL) and the resulting solution is added over 20 min. The mixture is stirred while allowing the bath to expire, and then for 18 h. Water (180 mL) is added at a continuous rate over 30 min. The suspension is stirred for 1 h, and then collected by vacuum filtration onto a medium porosity fritted funnel. The filter cake is washed with water (160 mL) and suction dried under nitrogen to give [(2R)-7-nitro-2,3-dihydro-1,4-benzodioxin-2-yl]methyl 4-methylbenzenesulfonate (19.68 g, 81% two steps) as a brown solid; m.p. 138° C. LCMS (Standard Method): 2.78 min, 388 (M+Na)$^+$. $^1$H NMR (300 MHz, DMSO-d6) δ7.79-7.72 (m, 3H), 7.49-7.42 (m, 3H), 7.06 (d, J=8.8 Hz, 1H), 4.59-4.55 (m, 1H), 4.41 (dd, J=2.6, 11.6 Hz, 2H), 4.22 (dd, J=6.3, 11.5 Hz, 1H), 4.12 (dd, J=6.8, 11.7 Hz, 1H) 2.38 (s, 3H).

D. Preparation of N-benzyl-1-[7-nitro-2,3-dihydro-1,4-benzodioxin-2-yl]methanamine

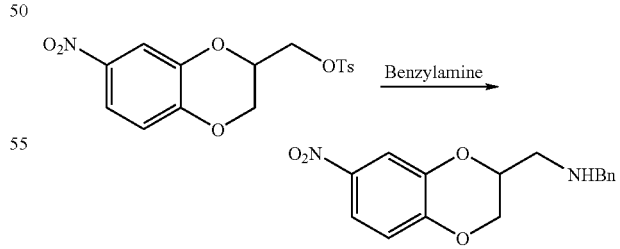

A 200 mL round bottomed flask equipped with a magnetic stir bar is charged with [7-nitro-2,3-dihydro-1,4-benzodioxin-2-yl]methyl 4-methylbenzenesulfonate (40.0 g, 110 mmol) and benzylamine (35.2 g, 328 mmol). The mixture is heated to 95° C. for 3 h, and then heating is discontinued. Once the temperature of the solution is 80° C., heptane (300 mL) is added slowly, with rapid stirring. Once the suspension is cooled to rt, the solid is collected by vacuum filtration, and the filter cake is washed several times with heptane and suction dried to give the title compound (32.55 g, 100%) as a yellow powder. LCMS (Basic Method): 1.93 min, 301 (M+H)+. $^1$H NMR (300 MHz, DMSO-d6) δ 7.77-7.70 (m, 1H), 7.47-7.18 (m, 6H), 7.10-7.06 (m, 1H), 4.47 (dd, J=2.5, 11.5 Hz, 1H), 4.37-4.29 (m, 1H), 4.15 (dd, J=7.1, 11.5 Hz, 1H), 3.73 (s, 2H), 2.43 (br s, 1H), 2.82-2.70 (m, 2H).

E. Preparation of (2S)-N-benzyl-1-[7-nitro-2,3-dihydro-1,4-benzodioxin-2-yl]methanamine

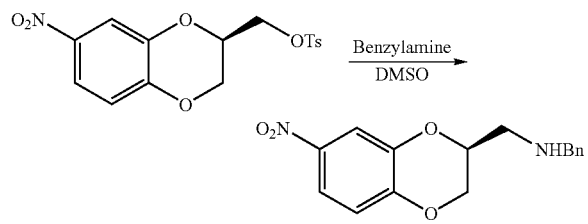

A 3 L three necked flask equipped with a heating mantle, thermocouple and mechanical stirrer is charged with [7-nitro-2,3-dihydro-1,4-benzodioxin-2-yl]methyl 4-methylbenzenesulfonate (356.8 g, 0.977 mol), DMSO (1 L) and benzylamine (261.7 g, 2.44 mol). The slurry is heated to maintain an internal temperature of 90° C. Heating is continued for 18 h, and then the solution is allowed to cool to 30° C. over 2 h. Water (400 mL) is added over 15 min. then seed crystals (~100 mg) are added resulting in rapid formation of a precipitate. The slurry is stirred for 30 min prior to additional water (2 L) being added over 1.5 h. The slurry is stirred for 4 h, the solids are collected by vacuum filtration, washed with water (2 L) and suction dried under nitrogen giving the title compound (302.87 g, 103%) as a yellow powder (94% ee). Yield is high due to trapped water, m.p. 98° C. (dried sample). LCMS (Basic Method): 2.05 min, 301 (M+H)+. $^1$H NMR (300 MHz, DMSO-d6) δ 7.77-7.70 (m, 1H), 7.47-7.18 (m, 6H), 7.10-7.06 (m, 1H), 4.47 (dd, J=2.5, 11.5 Hz, 1H), 4.37-4.29 (m, 1H), 4.15 (dd, J=7.1, 11.5 Hz, 1H), 3.73 (s, 2H), 2.82-2.70 (m, 2H), 2.43 (br s, 1H).

F. Enantiomeric enrichment of (2S)-N-benzyl-1-[7-nitro-2,3-dihydro-1,4-benzodioxin-2-yl]methanamine Step 1: Preparation of N-benzyl-1-[(2S)-7-nitro-2,3-dihydro-1,4-benzodioxin-2-yl]methanamine-(2S)-hydroxy(phenyl)acetic acid (1:1)

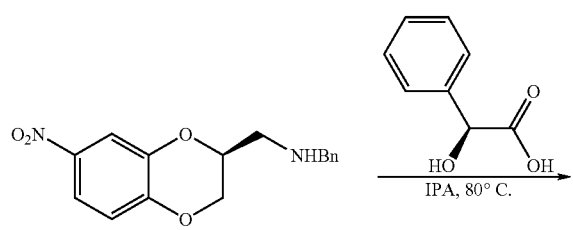

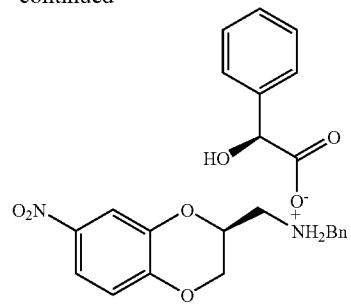

A 5 L three necked flask equipped with a mechanical stirrer, thermocouple and heating mantle is charged with N-benzyl-1-[(2S)-7-nitro-2,3-dihydro-1,4-benzodioxin-2-yl]methanamine (145 g, 0.484 mol, 93% ee) and isopropanol (2700 mL). The slurry is heated to 80° C. (solution is obtained ~60° C.) at which point solid (S)-Mandelic acid (73.64 g, 0.484 mol) is added in one portion. Heating is discontinued, and the solution is allowed to cool slowly. Seed crystals are added when the internal temperature reaches 66° C., initiation of crystallization is well established by at 56° C. The slurry is allowed to continue cooling to room temperature overnight.

Some of the material oils out and solidifies overnight. The slurry is heated to 55° C. for 18 h, and allowed to cool to room temperature. The solids are collected by vacuum filtration, washed with isopropanol (1 L) and suction dried under nitrogen to give the title compound (168 g, 77%) as an off-white powder (99% ee); m.p. 134° C. Anal. calcd for $C_{24}H_{24}N_2O_7$: C 63.71; H 5.35; N 6.19. Found: C 63.60; H 5.26; N 6.11.

Step 2: Free basing of N-benzyl-1-[(2S)-7-nitro-2,3-dihydro-1,4-benzodioxin-2-yl]methanamine-(2S)-hydroxy(phenyl)acetic acid (1:1)

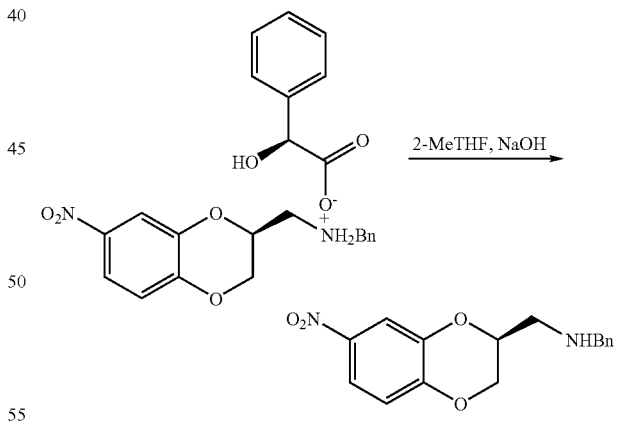

A 1 L round bottomed flask equipped with a magnetic stir bar is charged with solid N-benzyl-1-[(2S)-7-nitro-2,3-dihydro-1,4-benzodioxin-2-yl]methanamine-(2S)-hydroxy(phenyl)-acetic acid (1:1) (99% ee) (50.00 g, 112.2 mmol) and 2-methyltetrahydrofuran (330 mL). To the stirred suspension is added 1 N NaOH (115 mL, 115 mmol), and the biphasic mixture is stirred for 30 min. The layers are separated; the organic layer is washed with water (30 mL) and then with half saturated brine (30 mL). The solution is evaporated to dryness giving the title compound as a tan solid (33.05 g, 98%) (99% ee). $^1$H NMR (300 MHz, DMSO-d6) δ 7.77-7.70 (m, 1H), 7.47-7.18 (m, 6H), 7.10-7.06 (m, 1H), 4.47 (cid, J=2.5, 11.5 Hz, 1H), 4.37-4.29 (m, 1H), 4.15 (dd, J=7.1, 11.5 Hz, 1H), 3.73 (s, 2H), 2.82-2.70 (m, 2H), 2.43 (br s, 1H).

G. Preparation of {3-[benzylamino)methyl]-6-nitro-2,3-dihydro-1,4-benzodioxin-5-yl}acetonitrile

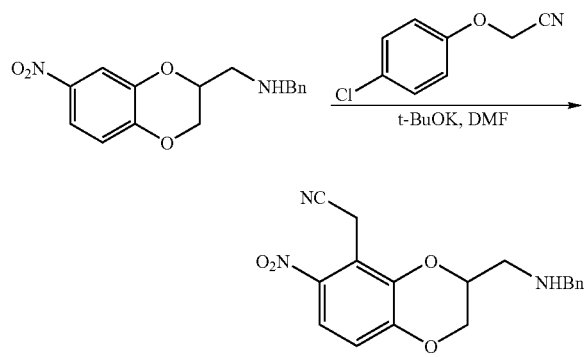

A 100 mL round bottomed flask equipped with a magnetic stir bar is charged with solid potassium t-butoxide (1.27 g, 11.3 mmol) and DMF (12 mL). The stirred solution is cooled until the internal temperature is 0° C., and a DMF (8 mL) solution containing N-benzyl-1-[7-nitro-2,3-dihydro-1,4-benzodioxin-2-yl]methanamine (0.85 g, 2.83 mmol) and (4-chlorophenoxy)acetonitrile (0.50 g, 2.96 mmol) is added dropwise. After 3 h, a 3 N aqueous solution of HCl is added until pH 1 is obtained. The solution is transferred to a separatory funnel and extracted with MTBE (25 mL). The aqueous phase is adjusted to pH 12 by the addition of 10 N aqueous NaOH, then extracted with CH$_2$Cl$_2$ (25 mL). The organics are washed with water (3×15 mL), and the volatiles are removed by evaporation to give the title compound (0.56 g, 58%). LCMS (Basic Method): 1.85 min, 340 (M+H)$^+$. $^1$H NMR (300 MHz, DMSO-d6) δ 7.71 (d, J=9.1 Hz, 1H), 7.35-7.17 (m, 5H), 7.10 (d, J=9.1 Hz, 1H), 4.50-4.37 (m, 2H), 4.16 (dd, J=7.0, 11.4 Hz, 1H), 4.10 (s, 2H), 3.76 (s, 2H), 2.87-2.74 (m, 2H), NH not observed.

H. Preparation of {(3S)-3-[(benzylamino)methyl]-6-nitro-2,3-dihydro-1,4-benzodioxin-5-yl}acetonitrile

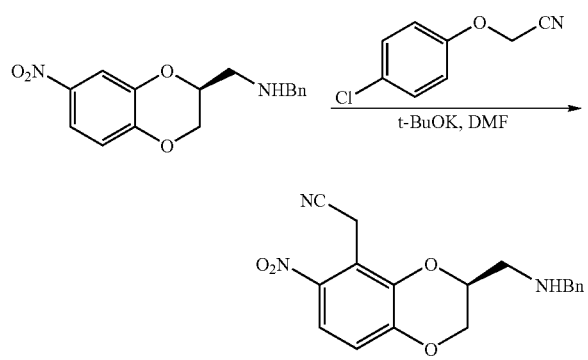

A 250 mL round bottomed flask equipped with a magnetic stir bar is charged with solid 95% potassium t-butoxide (1.57 g, 13.5 mmol) and DMF (6.5 mL), and the suspension is stirred until all the solids are dissolved. A DMF (4.0 mL) solution containing N-benzyl-1-[(2S)-7-nitro-2,3-dihydro-1,4-benzodioxin-2-yl]methanamine (1.00 g, 3.3 mmol) and (4-chlorophenoxy)acetonitrile (1.12 g, 6.7 mmol) is added over 3 min. After 30 min, a 2 N aqueous solution of HCl is added until pH 1 is obtained (~9 mL). The solution is transferred to a separatory funnel and extracted with toluene (2×10 mL) and discarded. The product-containing aqueous phase is adjusted to pH 10 by the addition of 10 N aqueous NaOH, and extracted with toluene (2×10 mL). The product-containing organic phases are combined and washed with water (15 mL) and then with brine (15 mL), and the volatiles are removed by evaporation to give the title compound (1.01 g, 88%) as a syrup. LCMS (Basic Method): 2.06 min, 340 (M+H)$^+$. $^1$H NMR (300 MHz, DMSO-d6) δ 7.71 (d, J=9.1 Hz, 1H), 7.35-7.17 (m, 5H), 7.10 (d, J=9.1 Hz, 1H), 4.50-4.37 (m, 2H), 4.16 (dd, J=7.0, 11.4 Hz, 1H), 4.10 (s, 2H), 3.76 (s, 2H), 2.87-2.74 (m, 2H), NH not observed.

I. Preparation of {(3S)-3-[(benzylamino)methyl]-6-nitro-2,3-dihydro-1,4-benzodioxin-5-yl}acetic acid.HCl

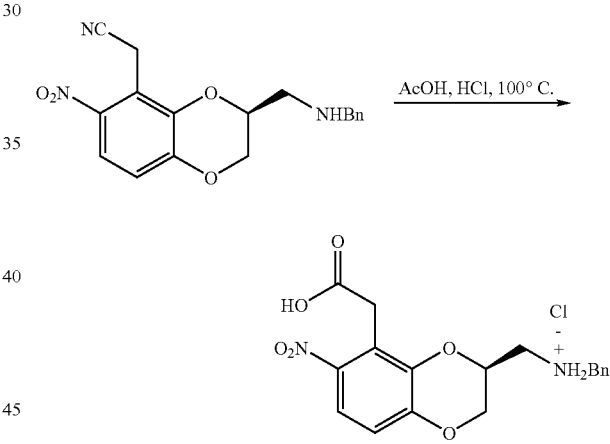

A 100 mL round bottomed flask equipped with a magnetic stir bar is charged with {(3S)-3-[(benzylamino)methyl]-6-nitro-2,3-dihydro-1,4-benzodioxin-5-yl}acetonitrile (10.00 g, 29.4 mmol) and glacial acetic acid (7.5 mL, 131 mmol). To the stirred solution is added 37% hydrochloric acid (15.0 mL, 180 mmol). The flask is immersed in an oil bath and heated to 100° C. for 6 h. The slurry is cooled to room temperature, water (15 mL) is added and the slurry is stirred for another 20 min. The precipitate is collected by vacuum filtration, washed with water (20 mL) and suction dried under nitrogen to give {(3S)-3-[(benzylamino)methyl]-6-nitro-2,3-dihydro-1,4-benzodioxin-5-yl}acetic acid.HCl (8.59 g, 74%) as a tan solid. mp 206° C.; LCMS (Basic Method): 1.99 min, 359 (M+H)$^+$. $^1$NMR (300 MHz, DMSO-d6) δ 9.90 (br s, 2H), 7.71 (d, J=9.6 Hz, 1H), 7.60-7.57 (m, 2H), 7.45-7.40 (m, 3H), 7.06 (d, J=9.6 Hz, 1H), 4.80-4.75 (m, 1H), 4.49 (dd, J=2.3, 11.7 Hz, 1H), 4.31-4.06 (n, 5H), 3.36-3.17 (m, 2H).

J. Preparation of (2S)-2-[(benzylamino)methyl]-2,3,8,9-tetrahydro-7H-[1,4]dioxino[2,3-e]indol-8-one (2E)-but-2-enedioate

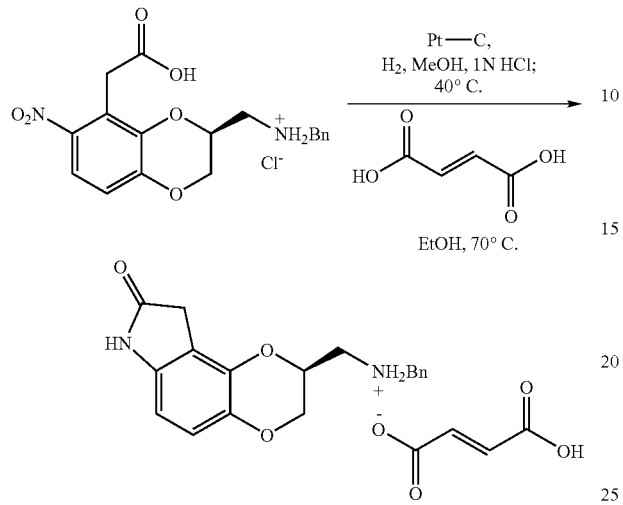

A 50 mL two necked flask equipped with a magnetic stir bar, gas inlet adapter and gas outlet adapter is charged with {(3S)-3-[(benzylamino)methyl]-6-nitro-2,3-dihydro-1,4-benzodioxin-5-yl}acetic acid.HCl (1.00 g, 2.53 mmol), methanol (20 mL), 1 N hydrochloric acid (2.53 mL, 2.53 mmol) and platinum (5% on carbon, 62% w/w water, 0.20 g). The flask head space is flushed with hydrogen gas (200 mL), the gas outlet adapter is closed and the slurry is stirred under a hydrogen atmosphere. After ~1 h, no solid {(3S)-3-[benzylamino)methyl]-6-nitro-2,3-dihydro-1,4-benzodioxin-5-yl}acetic acid.HCl is visible. The mixture is stirred for an additional 1 h under hydrogen, at which point the reaction is complete by LCMS. The catalyst is removed by vacuum filtration, and the resulting solution is heated to 45° C. (external) in an oil bath for 8 h. The volatiles are removed by rotary evaporation to give a pink solid. The solids are suspended in 2-methyl tetrahydrofuran (18 mL) and water (3 mL). 1 N NaOH is added until the solids dissolved and the pH of the aqueous phase is 10 (pH paper), about 6 mL is required. The aqueous layer is removed, and the organic phase is washed with water (4 mL) and half saturated brine (3 mL). The volatiles are removed by rotary evaporation to give a brown syrup. The syrup is dissolved in absolute ethanol (3 mL) and evaporated to dryness. Absolute ethanol (3 mL) is added to the residue and removed by rotary evaporation to give crude (2S)-2-[(benzylamino)methyl]-2,3,8,9-tetrahydro-7H-[1,4]dioxino[2,3-e]indol-8-one as a brown syrup.

Crude (2S)-2-[(benzylamino)methyl]-2,3,8,9-tetrahydro-7H-[1,4]dioxino[2,3-e]indol-8-one from above (~2.53 mmol) is dissolved in EtOH (16 mL) and heated under nitrogen to 70° C. (external) in an oil bath. Solid fumaric acid (0.29 g, 2.53 mmol) is added in one portion to the hot solution, and the heat is turned off. The solution becomes cloudy once the oil bath has cooled to 50° C. Seed crystals (5 mg) are introduced and the mixture is allowed to continue cooling to rt over 1.5 h. The slurry is further cooled to 5° C. (internal) by immersion in an ice water bath, held at this temperature for 1.5 h and collected by vacuum filtration. The filter cake is washed with cold EtOH (10 mL) and dried under suction giving the title compound (0.83 g, 77% from {(3S)-3-[(benzylamino)methyl]-6-nitro-2,3-dihydro-1,4-benzodioxin-5-yl}acetic acid.HCl) as a tan powder. LCMS (Basic Method): 1.83 min, 311 (M+H)⁺. ¹H NMR (300 MHz, DMSO-d6) δ 10.17 (br s, 1H), 7.38-7.21 (m, 5H), 6.66 (d, J=8.2 Hz, 1H), 6.57 (s, 2H), 6.28 (d, J=8.2 Hz, 1H), 4.35-4.33 (m, 1H), 4.25 (dd, J=2.2, 11.7 Hz, 1H), 3.96 (dd, J=6.4, 11.5 Hz, 1H), 3.83 (s, 2H), 3.32 (s, 2H), 2.83-2.81 (m, 2H), NH, and two OH's not observed.

K. Preparation of ethyl{(3S)-3-[(benzylamino)methyl]-6-nitro-2,3-dihydro-1,4-benzodioxin-5-yl}acetate

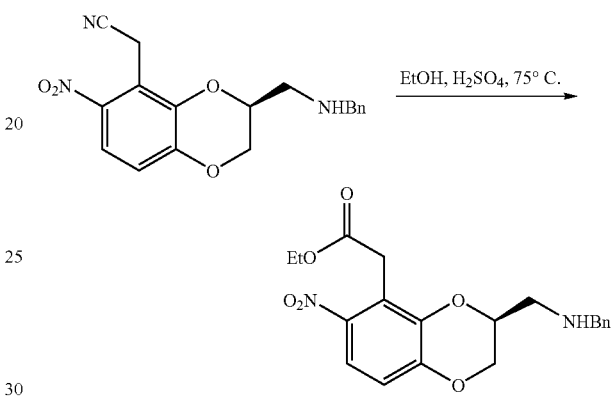

A 100 mL round bottomed flask equipped with a magnetic stir bar is charged {(3S)-3-[(benzylamino)methyl]-6-nitro-2,3-dihydro-1,4-benzodioxin-5-yl}acetonitrile (5.00 g, 14.5 mmol) and 95% ethanol (7.5 mL). To the stirred solution is added 95% sulfuric acid (5.0 mL, 89.0 mmol). The flask is immersed in an oil bath and heated to 75° C. for 4 days. The solution is cooled to room temperature and absolute ethanol (42.5 mL) is added. The reaction mixture is adjusted to pH 10 by the addition of 28% ammonium hydroxide (~12 mL), and the resulting slurry is stirred for 3 h. The precipitate is removed by vacuum filtration and the volatiles are evaporated giving crude title compound (6.02 g, 106%) as a red syrup. LCMS (Basic Method): 2.33 min, 387 (M+H)⁺.

L. Preparation of (2S)-2-[(benzylamino)methyl]-2,3,8,9-tetrahydro-7H-[1,4]dioxino[2,3-e]indol-8-one

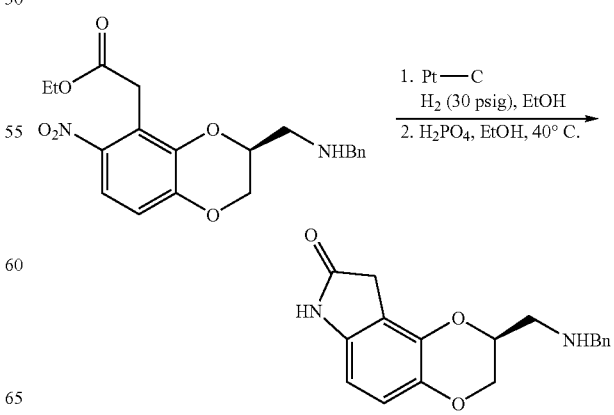

In a 500 mL Parr shake flask is charged crude ethyl {(3S)-3-[(benzylamino)methyl]-6-nitro-2,3-dihydro-1,4-benzodioxin-5-yl}acetate (6.02 g, 14.5 mmol), ethanol (50 mL) and Pt—C (5% on carbon, 50% w/w water, 1.0 g). The flask is pressurized to 30 psig and shaken for 18 h. The pressure is released, the catalyst is removed by filtration through celite, and ethanol (20 mL) is used to rinse the filter cake. To the solution is added 85% $H_3PO_4$ (1.21 mL, 17.4 mmol) and the mixture is heated to 40° C. for 36 h. The solution is filtered through celite and the volatiles are removed. The residue is suspended in isopropyl acetate (50 mL), THF (25 mL) and 1 N NaOH is added until pH 10 is obtained. The organic extracts are washed with water and then with brine treated with Darco 12-20Li (0.5 g), filtered through celite and evaporated giving crude title compound (2.50 g, 55%) as a red-orange syrup. LCMS (Basic Method): 1.84 min, 311 (M+H)$^+$. $^1$H NMR (400 MHz, CDCl$_3$) δ 10.4 (br s, 1H), 7.35-7.27 (m, 5H), 6.73 (d, J=8.3 Hz, 1H), 6.36 (d, J=8.3 Hz, 1H), 4.37-4.35 (m, 1H), 4.25 (dd, J=2.2, 11.5 Hz, 1H), 4.03 (dd, J=7.3, 11.5 Hz, 1H), 3.88 (s, 2H), 3.44 (s, 2H), 2.97-2.88 (m, 2H), 8.9 (br s, 1H).

M. Preparation of {(3S)-3-[(benzylamino)methyl]-6-nitro-2,3-dihydro-1,4-benzodioxin-5-yl}acetonitrile oxalate

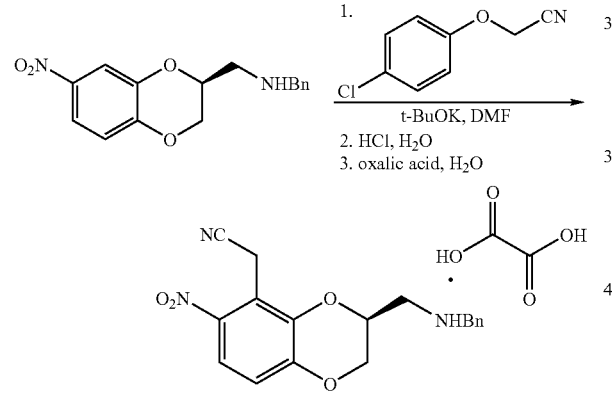

A 250 mL 3-neck round bottom flask equipped with an overhead stirrer, thermocouple, and addition funnel is charged with potassium tert-butoxide (95%, 7.87 g, 66.6 mmol) and DMF (30 mL) under N$_2$. Stirring the mixture at rt yields a clear solution. This is Solution A.

A separate 50 mL round bottom flask is charged with benzyl-(7-nitro-2,3-dihydro-benzo[1,4]dioxin-2-ylmethyl)-amine (5.0 g, 16.65 mmol), 4-chlorophenoxyacetonitrile (98%, 5.69 g, 33.3 mmol), and DMF (20 mL) under N$_2$. Manual swirling of the mixture accompanied by gentle heating with a heat gun yields a solution. This is Solution B. This solution is transferred to the addition funnel attached to the 250 mL flask.

Solution A is chilled to 12° C. (i.t.) with a crushed ice-water bath, and then Solution B is added dropwise to Solution A at such a rate as to maintain an i.t. of 12-16° C. The resulting deep purple reaction mixture is stirred at 12° C.

After 30 min, the reaction mixture is diluted with toluene (25 mL), and 2 N HCl (59 mL, 118 mmol) is added dropwise via an addition funnel at such a rate as to maintain an i.t. below 21° C. The resulting biphasic mixture is stirred vigorously for 5 min and then poured into a 250 mL separatory funnel. The layers are allowed to separate, and the bottom, product-containing, aqueous DMF layer is drained back into the 250 mL 3-neck round bottom flask.

Next, a solution of oxalic acid dihydrate (2.11 g, 16.7 mmol) in water (20 mL) is added dropwise, with stirring, at rt, to the aq DMF solution. The resulting slurry is stirred at rt for 18 h, and then at 0° C. for 1 h. The slurry is filtered on a 150 mL medium frit Büchner funnel. The cake is washed with water (2×50 mL) and dried under suction and a blanket of N$_2$ to yield 4.25 g (59%) of {(3S)-3-[(benzylamino)methyl]-6-nitro-2,3-dihydro-1,4-benzodioxin-5-yl}acetonitrile oxalate as a tan powder. $^1$H NMR (400 MHz, DMSO-d$_6$) δ 7.78 (d, J=9.2 Hz, 1H), 7.53-7.51 (m, 2H), 7.45-7.37 (m, 3H), 7.17 (d, J=9.1 Hz, 1H), 4.75 (m, 1H), 4.51 (dd, J=11.7, 2.5 Hz, 1H), 4.30-4.15 (m, 5H), 3.28, 3.22 (ABX, J$_{AB}$=13.5 Hz, J$_{BX}$=8.4 Hz, 2H). Anal. Calcd for C$_{20}$H$_{19}$N$_3$O$_8$: C, 55.94; H, 4.46; N, 9.79. Found: C, 56.26; H, 4.46; N, 9.67.

N. Preparation of (2S)-2-[(benzylamino)methyl]-2,3,8,9-tetrahydro-7H-[1,4]dioxino[2,3-e]indol-8-one 4-methylbenzenesulfonate

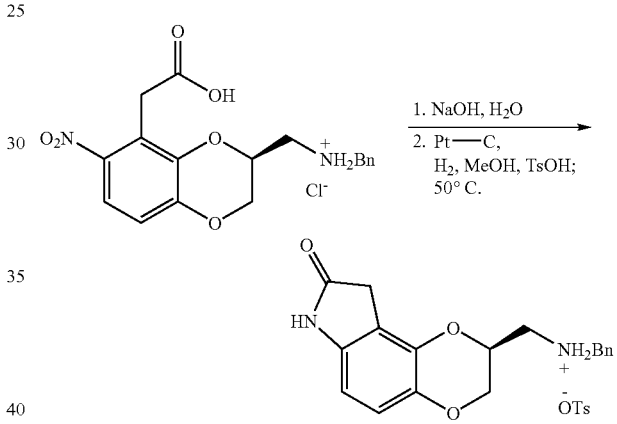

Step 1: A 10 mL round bottomed flask equipped with a magnetic stir bar is charged with {(3S)-3-[(benzylamino)methyl]-6-nitro-2,3-dihydro-1,4-benzodioxin-5-yl}acetic acid.HCl (2.00 g, 5.07 mmol) and water (5.0 mL). To the slurry is added 1 N NaOH (5.07 mL, 5.07 mmol) and the slurry is stirred for 1 h. The solids are collected by vacuum filtration, washed with water (10 mL) and suction dried under nitrogen, to give {(3S)-3-[(benzylamino)methyl]-6-nitro-2,3-dihydro-1,4-benzodioxin-5-yl}acetic acid (1.71 g, 94%) as a tan powder.

Step 2: A 50 mL two necked flask equipped with a magnetic stir bar, gas inlet adapter and gas outlet adapter is charged with {(3S)-3-[(benzylamino)methyl]-6-nitro-2,3-dihydro-1,4-benzodioxin-5-yl}acetic acid [from above (1.36 g, 3.80 mmol)], methanol (20 mL), and p-toluenesulfonic acid monohydrate (1.80 g, 9.5 mmol) and platinum (5% on carbon, 62% w/w water, 0.27 g). The flask head space is flushed with hydrogen gas (100 mL), the gas outlet adapter is closed and the slurry is stirred under a hydrogen atmosphere for 18 h under hydrogen, at which point the reaction is complete by LCMS. The catalyst is removed by vacuum filtration, and the resulting solution is heated to 50° C. (external) in an oil bath for 48 h. The solids are collected by vacuum filtration, the filter cake is washed with cold MeOH (10 mL) and dried under nitrogen giving (2S)-2-[(benzylamino)methyl]-2,3,8, 9-tetrahydro-7H-[1,4]dioxino[2,3-e]indol-8-one 4-methylbenzenesulfonate (1.12 g, 61%) as an off-white powder.

O. Preparation of (2S)-2-[(benzylamino)methyl]-2,3,8,9-tetrahydro-7H-[1,4]-dioxino[2,3-e]indol-8-one (2E)-but-2-enedioate Step 1: (2S)-2-[(benzylamino)methyl]-2,3,8,9-tetrahydro-7H-[1,4]dioxino[2,3-e]indol-8-one 4-methylbenzenesulfonate (0.75 g, 1.54 mmol) is suspended in 2-methyl tetrahydrofuran (10 mL), 1 N NaOH is added until the solids dissolve and the pH of the aqueous phase is 10 (pH paper), about 1.6 mL is required. The aqueous layer is removed, and the organic phase is washed with water (2×2 mL). The volatiles are removed by rotary evaporation to give a yellow syrup. The syrup is dissolved in absolute ethanol (3 mL) and evaporated to dryness. Absolute ethanol (3 mL) is added to the residue and removed by rotary evaporation to give crude (2S)-2-[(benzylamino)methyl]-2,3,8,9-tetrahydro-7H-[1,4]dioxino[2,3-e]indol-8-one as a yellow syrup which is carried directly into the next step.

Step 2: (2S)-2-[(benzylamino)methyl]-2,3,8,9-tetrahydro-7H-[1,4]dioxino[2,3-e]indol-8-one from above (~1.54 mmol) is dissolved in EtOH (10 mL) and heated under nitrogen to 80° C. (external) in an oil bath. Solid fumaric acid (0.18 g, 1.54 mmol) is added in one portion to the hot solution, and the heat is turned off. The solution becomes cloudy once the oil bath has cooled to 75° C. the mixture is allowed to continue cooling to rt over 2.5 h. The solids are collected by vacuum filtration, the filter cake is washed with cold EtOH (10 mL) and dried under nitrogen giving the title compound (0.83 g, 84% (from step 1) as an off-white powder. LCMS (Basic Method): 1.83 min, 311 (M+H)⁺. $^1$H NMR (300 MHz, DMSO-d6) δ 10.17 (br s, 1H). 7.38-7.21 (m, 5H), 6.66 (d, J=8.2 Hz, 1H), 6.57 (s, 2H), 6.28 (d, J=8.2 Hz, 1H), 4.35-4.33 (m, 1H), 4.25 (dd, J=2.2, 11.7 Hz, 1H), 3.96 (dd, J=6.4, 11.5 Hz, 1H), 3.83 (s, 2H), 3.32 (s, (2H), 2.83-2.81 (m, 2H), NH, and two OH's not observed.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of Formula 4 or a salt or hydrate thereof:

Formula 4 wherein:
n is the integer 0 or 1;
PG is an optionally substituted benzyl; and
$R_3$ is a ring substituent chosen from hydroxy, $C_1$-$C_6$haloalkyl, $C_1$-$C_6$haloalkoxy, $C_1$-$C_6$alkyl, $C_1$-$C_6$alkoxy, $C_1$-$C_6$alkanoyloxy, amino, mono- or di-($C_1$-$C_6$alkyl)amino, mono- or di-($C_1$-$C_6$alkyl)aminocarbonyl and $C_1$-$C_6$alkylaminosulfonyl.

2. A compound or salt or hydrate thereof according to claim 1, wherein the compound is (R)-2-((2-(benzyloxy)-4-nitrophenoxy)methyl)oxirane.

3. A process for preparing a compound of Formula 5 or a salt or hydrate thereof:

Formula 5 wherein:
n is the integer 0 or 1; and
$R_3$ is a ring substituent chosen from hydroxy, $C_1$-$C_6$haloalkyl, $C_1$-$C_6$haloalkoxy, $C_1$-$C_6$alkyl, $C_1$-$C_6$alkoxy, $C_1$-$C_6$alkanoyloxy, amino, mono- or di-($C_1$-$C_6$alkyl)amino, mono- or di-($C_1$-$C_6$alkyl)aminocarbonyl and $C_1$-$C_6$alkylaminosulfonyl;
comprising cyclizing a compound of Formula 4 or a salt or hydrate thereof:

Formula 4 wherein PG is an optionally substituted benzyl;
for a time and under conditions effective to provide the compound of Formula 5 or a salt or hydrate thereof.

4. A process according to claim 3, further comprising the step of alkylating a compound of Formula 3 or a salt or hydrate thereof:

Formula 3 with an alkylating agent of Formula:

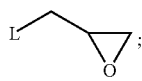

wherein L is a leaving group;
for a time and under conditions effective to provide the compound of Formula 4 or salt or hydrate thereof.

5. A process according to claim 4, wherein the compound of Formula 4 is (R)-2-((2-(benzyloxy)-4-nitrophenoxy)methyl)oxirane, and the compound of Formula 5 is (S)-(7-nitro-2,3-dihydrobenzo[b][1,4]dioxin-2-yl)methanol.

6. A compound of Formula 7 or Formula 8 or a salt or hydrate of Formula 7 or Formula 8:

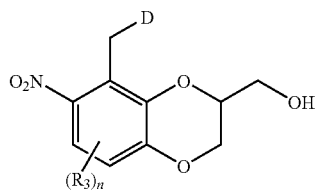

Formula 7

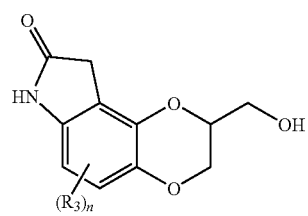

Formula 8 wherein:
n is the integer 0 or 1;
D is COOH or —COOR$_w$;
R$_w$ is C$_1$-C$_8$alkyl; and
R$_3$ is a ring substituent chosen from hydroxy, halogen, C$_1$-C$_6$haloalkyl, C$_1$-C$_6$haloalkoxy, C$_1$-C$_6$alkyl, C$_1$-C$_6$alkoxy, C$_1$-C$_6$alkanoyloxy, amino, mono- or di-(C$_1$-C$_6$alkyl)amino, mono- or di-(C$_1$-C$_6$alkyl)aminocarbonyl and C$_1$-C$_6$alkylaminosulfonyl.

7. A process for preparing a compound of Formula 7 or a salt or hydrate thereof:

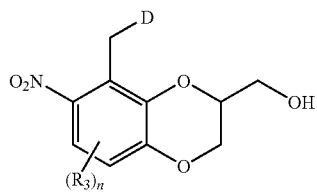

Formula 7 wherein:
n is the integer 0 or 1;
D is COOH or —COOR$_w$;
R$_w$ is C$_1$-C$_8$alkyl; and
R$_3$ is a ring substituent chosen from hydroxy, halogen, C$_1$-C$_6$haloalkyl, C$_1$-C$_6$haloalkoxy, C$_1$-C$_6$alkyl, C$_1$-C$_6$alkoxy, C$_1$-C$_6$alkanoyloxy, amino, mono- or di-(C$_1$-C$_6$alkyl)amino, mono- or di-(C$_1$-C$_6$alkyl)aminocarbonyl and C$_1$-C$_6$alkylaminosulfonyl;

comprising contacting a compound of Formula 6 or a salt or hydrate thereof:

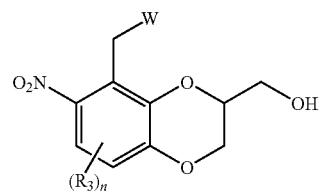

Formula 6 wherein:
W is CN or —COOR$_w$;
with water or a C$_1$-C$_8$alkanol for a time and under conditions effective to provide the compound of Formula 7 or a salt or hydrate thereof.

8. A process for preparing a compound of Formula 8 or a salt or hydrate thereof:

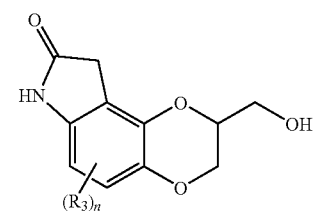

Formula 8 wherein:
n is the integer 0 or 1; and
R$_3$ is a ring substituent chosen from hydroxy, halogen, C$_1$-C$_6$haloalkyl, C$_1$-C$_6$haloalkoxy, C$_1$-C$_6$alkyl, C$_1$-C$_6$alkoxy, C$_1$-C$_6$alkanoyloxy, amino, mono- or di-(C$_1$-C$_6$alkyl)amino, mono- or di-(C$_1$-C$_6$ alkyl)amino carbonyl and C$_1$-C$_6$alkylaminosulfonyl;

comprising reducing and cyclizing a compound of Formula 7 or a salt or hydrate thereof:

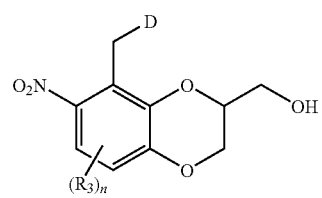

Formula 7 wherein:
D is COOH or —COOR$_w$; and
R$_w$ is C$_1$-C$_8$alkyl;
for a time and under conditions effective to provide the compound of Formula 8 or a salt or hydrate thereof.

9. A process for preparing a compound of Formula 9 or a salt or hydrate thereof:

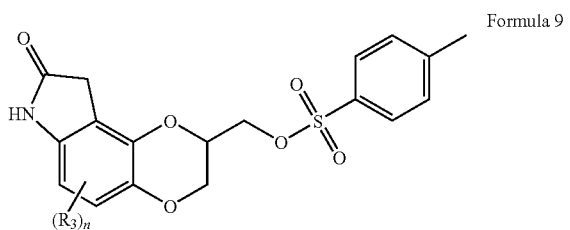

wherein:

n is the integer 0 or 1; and

R₃ is a ring substituent chosen from hydroxy, halogen, $C_1$-$C_6$haloalkyl, $C_1$-$C_6$haloalkoxy, $C_1$-$C_6$alkyl, $C_1$-$C_6$alkoxy, $C_1$-$C_6$alkanoyloxy, amino, mono- or di-($C_1$-$C_6$alkyl)amino, mono- or di-($C_1$-$C_6$alkyl)aminocarbonyl and $C_1$-$C_6$alkylaminosulfonyl;

comprising:

contacting a compound of Formula 8 or a salt or hydrate thereof:

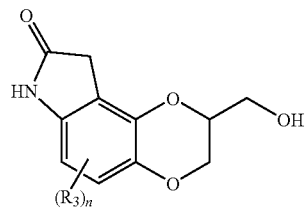

with toluenesulfonyl chloride for a time and under conditions effective to provide the compound of Formula 9 or a salt or hydrate thereof.

10. A process for preparing a compound of Formula A or a pharmaceutically acceptable salt or hydrate thereof:

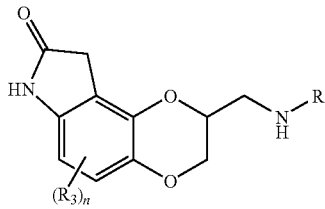

wherein:

n is the integer 0 or 1;

R is optionally substituted phenyl$C_1$-$C_2$alkyl; and

R₃ is a ring substituent chosen from hydroxy, halogen, $C_1$-$C_6$haloalkyl, $C_1$-$C_6$haloalkoxy, $C_1$-$C_6$alkyl, $C_1$-$C_6$alkoxy, $C_1$-$C_6$alkanoyloxy, amino, mono- or di-($C_1$-$C_6$alkyl)amino, mono- or di-($C_1$-$C_6$alkyl)aminocarbonyl and $C_1$-$C_6$alkylaminosulfonyl;

comprising:

contacting a compound of Formula 8 or a salt or hydrate thereof:

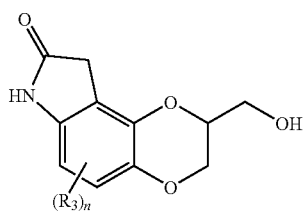

with toluenesulfonyl chloride for a time and under conditions effective to provide a compound of Formula 9 or a salt or hydrate thereof:

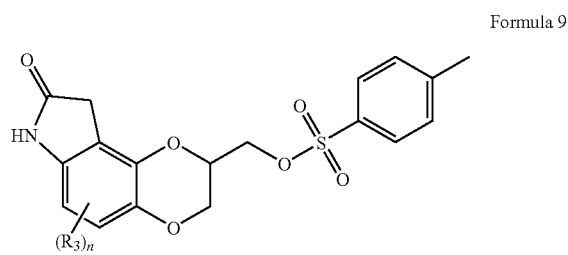

and contacting the compound of Formula 9 or salt or hydrate thereof with RNH₂ for a time and under conditions effective to provide the compound of Formula A or a pharmaceutically acceptable salt or hydrate thereof.

11. A process according to claim 10, wherein the compound of Formula A is:

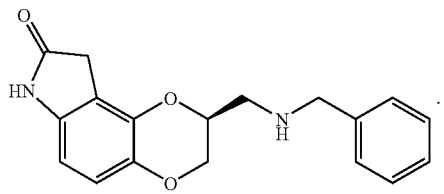 [SMILES: O=C1Cc2c(ccc3c2O[C@@H](CNCc2ccccc2)CO3)N1]

12. A compound of Formula 12 or a salt or hydrate thereof:

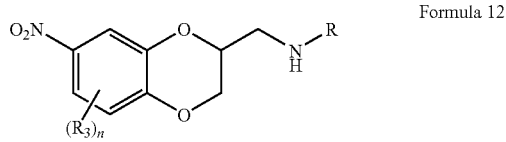

wherein:

n is the integer 0 or 1;

R is optionally substituted benzyl; and

R₃ is a ring substituent chosen from hydroxy, halogen, $C_1$-$C_6$haloalkyl, $C_1$-$C_6$haloalkoxy, $C_1$-$C_6$alkyl, $C_1$-$C_6$alkoxy, $C_1$-$C_6$alkanoyloxy, amino, mono- or di-($C_1$-$C_6$alkyl)amino, mono- or di-($C_1$-$C_6$alkyl)aminocarbonyl and $C_1$-$C_6$alkylaminosulfonyl.

13. A process comprising:

contacting a compound of Formula 12 or a salt or hydrate thereof:

Formula 12

[Structure: 6-nitro-benzodioxane with CH2-NH-R substituent, (R3)n on ring]

n is the integer 0 or 1;

R₃ is a ring substituent chosen from hydroxy, halogen, $C_1$-$C_6$haloalkyl, $C_1$-$C_6$haloalkoxy, $C_1$-$C_6$alkyl, $C_1$-$C_6$alkoxy, $C_1$-$C_6$alkanoyloxy, amino, mono- or di-($C_1$-$C_6$alkyl)amino, mono- or di-($C_1$-$C_6$alkyl)aminocarbonyl and $C_1$-$C_6$alkylaminosulfonyl; and R is optionally substituted benzyl;

with

[Structure: X-CH2-CN or X-CH2-COOR_w]

wherein $R_w$ is $C_1$-$C_8$alkyl and X is a leaving group;

for a time and under conditions effective to provide the compound of Formula 13 or a salt or hydrate thereof and thereby forming a compound of Formula 13

Formula 13

[Structure: 6-nitro-benzodioxane with CH2-W at 8-position and CH2-NH-R at 2-position, (R3)n]

wherein W is CN or $COOR_w$.

14. A process according to claim 13, further comprising the step of contacting a compound of Formula 11 or a salt or hydrate thereof:

Formula 11

[Structure: 6-nitro-benzodioxane with CH2-O-tosylate substituent, (R3)n]

with $RNH_2$ for a time and under conditions effective to provide the compound of Formula 12 or a salt or hydrate thereof.

15. A process of claim 13 additionally comprising contacting the compound of Formula 13 or a salt or hydrate thereof:

Formula 13

[Structure: 6-nitro-benzodioxane with CH2-W and CH2-NH-R, (R3)n]

wherein:

W is CN or —$COOR_w$; and $R_w$ is $C_1$-$C_8$alkyl;

with water or a $C_1$-$C_8$alkanol for a time and under conditions effective to provide the compound of Formula 14 or a salt or hydrate thereof

Formula 14

[Structure: 6-nitro-benzodioxane with CH2-C(O)-OR_x at 8-position and CH2-NH-R at 2-position, (R3)n]

wherein $R_x$ is hydrogen or $C_1$-$C_8$alkyl.

16. A process according to claim 15, further comprising the step of contacting a compound of Formula 12 or a salt or hydrate thereof:

Formula 12

[Structure: 6-nitro-benzodioxane with CH2-NH-R, (R3)n]

with

[Structure: X-CH2-CN or X-CH2-COOR_w]

wherein X is a leaving group;

for a time and under conditions effective to provide the compound of Formula 13 or a salt or hydrate thereof.

17. A process according to claim 10, further comprising the step of reducing and cyclizing a compound of Formula 7 or a salt or hydrate thereof:

Formula 7

[Structure: 6-nitro-benzodioxane with CH2-D at 8-position and CH2-OH at 2-position, (R3)n]

wherein:

D is COOH or —$COOR_w$; and $R_w$ is $C_1$-$C_8$alkyl;

for a time and under conditions effective to provide the compound of Formula 8 or a salt or hydrate thereof.

18. A process according to claim 17, further comprising the step of contacting a compound of Formula 6 or a salt or hydrate thereof:
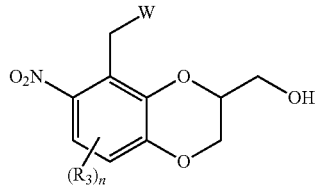
Formula 6
wherein W is CN or —COOR$_w$;
with water or a C$_1$-C$_8$alkanol for a time and under conditions effective to provide the compound of Formula 7 or a salt or hydrate thereof.
\* \* \* \* \*